US011382801B2

(12) United States Patent
Erdem et al.

(10) Patent No.: US 11,382,801 B2
(45) Date of Patent: Jul. 12, 2022

(54) ABSORBENT ARTICLES HAVING APERTURED, THREE-DIMENSIONAL MATERIALS AND METHODS FOR MAKING SAME

(71) Applicant: The Procter & Gamble Company, Cincinnati, OH (US)

(72) Inventors: Gueltekin Erdem, Beijing (CN); Sascha Kreisel, Schwalbach am Taunus (DE); Weidong Wu, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 841 days.

(21) Appl. No.: 16/142,161

(22) Filed: Sep. 26, 2018

(65) Prior Publication Data
US 2019/0105209 A1    Apr. 11, 2019

Related U.S. Application Data

(63) Continuation of application No. PCT/CN2017/105641, filed on Oct. 11, 2017.

(51) Int. Cl.
*A61F 13/512* (2006.01)
*A61F 13/537* (2006.01)
(Continued)

(52) U.S. Cl.
CPC .. *A61F 13/53713* (2013.01); *A61F 13/15203* (2013.01); *A61F 13/15707* (2013.01);
(Continued)

(58) Field of Classification Search
CPC .. A61F 13/511; A61F 13/5116; A61F 13/512; A61F 13/5121; A61F 13/5123;
(Continued)

(56) References Cited

U.S. PATENT DOCUMENTS

| | | | |
|---|---|---|---|
| 4,323,069 A * | 4/1982 | Ahr | A61F 13/512 604/378 |
| 4,324,246 A * | 4/1982 | Mullane | A61F 13/512 604/366 |

(Continued)

FOREIGN PATENT DOCUMENTS

| | | |
|---|---|---|
| CN | 101443499 A | 5/2009 |
| CN | 102673030 A | 9/2012 |

(Continued)

OTHER PUBLICATIONS

PCT International Search Report and Written Opinion, PCT/CN2017/105641, dated Apr. 7, 2019—9 pages.

(Continued)

*Primary Examiner* — Catharine L Anderson
(74) *Attorney, Agent, or Firm* — Daniel S. Albrecht; Christian M. Best

(57) ABSTRACT

An absorbent article is provided. The absorbent article includes a nonwoven, liquid permeable topsheet, a liquid impermeable backsheet, and an absorbent core disposed at least partially intermediate the topsheet and the backsheet. The topsheet includes a layer of fibers and has a plurality of apertures defined in the layer of fibers. At least some of the apertures have a side wall having a portion disposed an angle in the range of about 55 degrees to about 90 degrees, in the range of about 60 degrees to about 80 degrees, or in the range of about 63 degrees to about 75 degrees, according to the 2D X-Ray CT Scan Test herein.

22 Claims, 22 Drawing Sheets

(51) Int. Cl.

| | |
|---|---|
| *A61F 13/64* | (2006.01) |
| *A61F 13/84* | (2006.01) |
| *A61F 13/476* | (2006.01) |
| *A61F 13/15* | (2006.01) |
| *A61L 15/24* | (2006.01) |
| *A61L 15/26* | (2006.01) |
| *A61L 15/28* | (2006.01) |
| *A61F 13/56* | (2006.01) |
| *A61F 13/513* | (2006.01) |
| *A61F 13/53* | (2006.01) |

(52) U.S. Cl.
CPC ...... *A61F 13/15731* (2013.01); *A61F 13/476* (2013.01); *A61F 13/513* (2013.01); *A61F 13/5121* (2013.01); *A61F 13/5123* (2013.01); *A61F 13/565* (2013.01); *A61F 13/64* (2013.01); *A61F 13/84* (2013.01); *A61L 15/24* (2013.01); *A61L 15/26* (2013.01); *A61L 15/28* (2013.01); *A61F 2013/1513* (2013.01); *A61F 2013/15146* (2013.01); *A61F 2013/15406* (2013.01); *A61F 2013/51338* (2013.01); *A61F 2013/53024* (2013.01); *A61F 2013/53035* (2013.01); *A61F 2013/530255* (2013.01); *A61F 2013/530875* (2013.01); *A61F 2013/8497* (2013.01)

(58) Field of Classification Search
CPC ........ A61F 13/5126; A61F 2013/15284; A61F 2013/15406; A61F 2013/15495; A61F 2013/51165; A61F 2013/51178; A61F 2013/5127; A61F 2013/5128
See application file for complete search history.

(56) References Cited

U.S. PATENT DOCUMENTS

| | | | | |
|---|---|---|---|---|
| 4,846,813 A | * | 7/1989 | Raley | ............ A61F 13/512 604/385.08 |
| 5,356,405 A | | 10/1994 | Thompson et al. | |
| 5,648,142 A | * | 7/1997 | Phillips | ............ A61F 13/512 428/131 |
| 5,895,623 A | * | 4/1999 | Trokhan | ............ D04H 1/64 264/504 |
| 6,093,871 A | | 7/2000 | Takai et al. | |
| 6,383,441 B1 | | 5/2002 | Takai et al. | |
| 6,410,823 B1 | | 6/2002 | Daley et al. | |
| 9,242,406 B2 | | 1/2016 | Coe et al. | |
| 9,861,533 B2 | | 1/2018 | Hardie et al. | |
| 2003/0059574 A1 | | 3/2003 | Thomas | |
| 2003/0186026 A1 | | 10/2003 | Thomas | |
| 2003/0187417 A1 | | 10/2003 | Kudo et al. | |
| 2004/0127875 A1 | | 7/2004 | Hammons et al. | |
| 2005/0112323 A1 | | 5/2005 | Thomas | |
| 2007/0020434 A1 | | 1/2007 | Thomas | |
| 2012/0282436 A1 | | 11/2012 | Coe et al. | |
| 2014/0324009 A1 | | 10/2014 | Lee et al. | |
| 2014/0336605 A1 | | 11/2014 | Hardie et al. | |
| 2015/0250662 A1 | * | 9/2015 | Isele | ............ A61F 13/551 604/378 |
| 2016/0136003 A1 | | 5/2016 | Mullane et al. | |
| 2016/0136010 A1 | | 5/2016 | Roe et al. | |
| 2016/0136014 A1 | | 5/2016 | Arora et al. | |
| 2016/0136015 A1 | | 5/2016 | Giovanni et al. | |
| 2016/0136016 A1 | | 5/2016 | Mullane et al. | |
| 2016/0136919 A1 | | 5/2016 | Roe et al. | |
| 2016/0153128 A1 | | 6/2016 | Xie et al. | |
| 2018/0000654 A1 | | 1/2018 | Arora et al. | |
| 2018/0000655 A1 | | 1/2018 | Mullane et al. | |
| 2018/0000656 A1 | | 1/2018 | Roe et al. | |

FOREIGN PATENT DOCUMENTS

| | | |
|---|---|---|
| CN | 104994821 A | 10/2015 |
| JP | S51108943 A | 9/1976 |
| JP | H0363325 U | 6/1991 |
| JP | 2009-215667 | 9/2009 |
| JP | 2010-106430 | 5/2010 |
| JP | 2011132623 | 7/2011 |
| JP | 2011132623_TRAN | 7/2011 |
| WO | 2013163360 A2 | 10/2013 |
| WO | 2017033867 A1 | 3/2017 |

OTHER PUBLICATIONS

International Search Report and Written Opinion, PCT/CN2017/105641.

* cited by examiner

FIG. 24
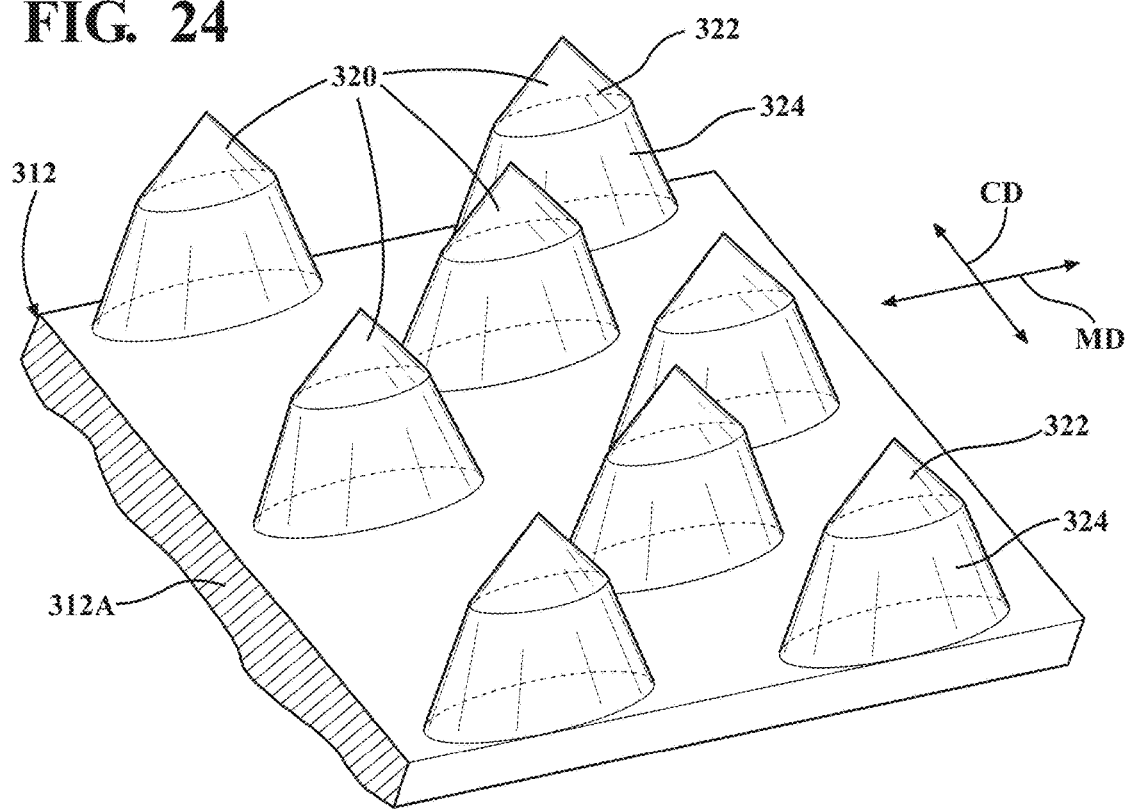
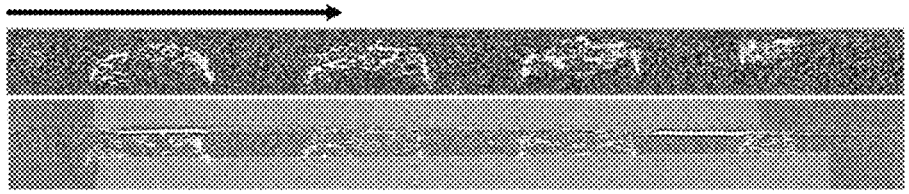
FIG. 27
5mm

ABSORBENT ARTICLES HAVING APERTURED, THREE-DIMENSIONAL MATERIALS AND METHODS FOR MAKING SAME

CROSS REFERENCE TO RELATED APPLICATION

This application is a continuation, under 35 U.S.C. § 120, of Patent Application No. PCT/CN2017/105641, filed on Oct. 11, 2017, which is herein incorporated by reference in its entirety.

FIELD

The present disclosure is directed to absorbent articles having apertured, three-dimensional materials and methods for making same.

BACKGROUND

Absorbent articles typically comprise a topsheet, a backsheet, and an absorbent core disposed at least partially between the topsheet and the backsheet. The absorbent article may also comprise an acquisition layer that temporarily stores liquid bodily exudates (e.g., runny bowel movements, urine, menses) received from the topsheet and an optional distribution layer that transfers and distributes the liquid bodily exudates from the acquisition layer to the absorbent core.

Many absorbent articles, including diapers, rely on capillary action to achieve liquid bodily exudate acquisition and wicking of the bodily exudates away from the skin of a wearer. The structure of absorbent articles generally results in a configuration in which there is a higher capillary pressure in the bottom layer and a lower capillary pressure in the top layer. Some absorbent articles also comprise textured and/or apertured topsheets to improve fluid handling properties.

Many topsheets are formed from hydrophilic materials to absorb liquid and transfer it away from skin. However, such hydrophilic topsheets retain liquid and stay wet which may not be preferred. Hydrophobic topsheets, formed from materials which may not retain liquid, are provided with apertures having large openings on a wearer-facing surface to enable effective liquid transfer from the wearer-facing surface to the absorbent core. Large openings, however, can come at the expense of reduced visual appeal and lower tactile softness. Further, when the large apertures are formed, long tails or side walls extend in a direction away from the wearer-facing surface. Also, the angles at which the side walls are formed are believed to be not steep. During use of the absorbent article having an aperture topsheet with long aperture side walls, compressive forces applied to the topsheet may cause the long side walls to collapse or fold inwardly towards the center of the aperture, thereby reducing the amount of fluid able to flow through the apertures.

Hence, current textured and/or aperture topsheets have disadvantages in softness, apertures remaining open under compression, and three dimensionality. Such topsheets should be improved.

SUMMARY

The present disclosure addresses the disadvantages of the current textured and/or apertured topsheets by providing improved softness, three-dimensionality, and apertures that remain open under compression, which is advantageous for hydrophobic topsheets. More specifically, the topsheet of the present disclosure is formed with at least some of the apertures having a steep side wall. By forming at least some of the apertures with a steep side wall, at least the following advantages result. First, a smaller wearer-facing opening area may be formed, causing less skin markings on the user, yet yield a similar bodily fluid flow rate through the aperture as that of a related art aperture having a larger wearer-facing opening area. Also, a smaller wearer-facing opening area results in a shorter tail or side wall, which is less likely to deform inwardly toward the aperture center and limit or block flow through the aperture. Wearer-facing opening areas are easy to form with very steep angles when the opening areas are smaller in size as the pins for forming apertures with smaller wearer-facing opening areas are shorter in length. As discussed further below, it is believed that when an aperture side wall is formed at a steep angle, the side wall is less likely to fold inwardly toward the center of the aperture to partially or substantially fully close the aperture.

In accordance with an aspect of the present disclosure, an absorbent article is provided comprising: a nonwoven, liquid permeable topsheet, a liquid impermeable backsheet, and an absorbent core disposed at least partially intermediate the topsheet and the backsheet. The topsheet comprises a layer of fibers and a plurality of apertures defined in the layer of fibers. The Basis Weight of the topsheet is in the range of about 10 gsm to about 35 gsm, about 15 gsm to about 30 gsm, about 18 gsm to about 25 gsm, or about 20 gsm to about 24 gsm, according to the Basis Weight Test herein. The topsheet has an Effective Open Area in the range of about 15% to about 30%, in the range of about 18% to about 25%, or in the range of about 20% to about 24%, according to the Aperture Test herein. The topsheet comprises a wearer-facing surface and a garment-facing surface, wherein at least some of the apertures have a wearer-facing opening area and a garment-facing opening area, and wherein the wearer-facing opening area is larger than the garment-facing opening area. At least some of the apertures comprise a side wall, wherein at least a portion of the side wall has an angle in the range of about 55 degrees to about 90 degrees, in the range of about 60 degrees to about 80 degrees, or in the range of about 63 degrees to about 75 degrees, according to the 2D X-Ray CT Scan Test herein. The garment-facing opening area of at least some of the apertures is in the range of about 1.0 mm$^2$ to about 7.5 mm$^2$, according to the 2D X-Ray CT Scan Test herein, and the wearer-facing opening area of at least some of the apertures is in the range of about 2 mm$^2$ to about 12 mm$^2$, according to the 2D X-Ray CT Scan Test herein. At least some of the apertures have a central major axis dimension and a central minor axis dimension, wherein the central major axis dimension is greater than 1.5 mm, when measured at the garment-facing opening area, according to the 2D X-Ray CT Scan Test herein.

In accordance with another aspect of the present disclosure, an absorbent article is provided comprising: a nonwoven, liquid permeable topsheet, a liquid impermeable backsheet, and an absorbent core disposed at least partially intermediate the topsheet and the backsheet. The topsheet comprises a layer of hydrophobic, carded fibers and a plurality of apertures defined in the layer of carded fibers. The Basis Weight of the topsheet is in the range of about 10 gsm to about 35 gsm, about 15 gsm to about 30 gsm, about 18 gsm to about 25 gsm, or about 20 gsm to about 24 gsm, according to the Basis Weight Test herein. The topsheet has an Effective Open Area in the range of about 15% to about 30%, in the range of about 18% to about 25%, or in the range of about 20% to about 24%, according to the Aperture Test herein. The topsheet comprises a wearer-facing surface and a garment-facing surface, wherein at least some of the apertures have a wearer-facing opening area and a garment-facing opening area, and wherein the wearer-facing opening area is larger than the garment-facing opening area. At least some of the apertures comprise a side wall, wherein at least a portion of the side wall has an angle in the range of about 55 degrees to about 90 degrees, in the range of about 60 degrees to about 80 degrees, or in the range of about 63 degrees to about 75 degrees, according to the 2D X-Ray CT scan Test herein. The garment-facing opening area of at least some of the apertures is in the range of about 1.0 mm$^2$ to about 7.5 mm$^2$, according to the 2D X-Ray CT Scan Test herein, and the wearer-facing opening area of at least some of the apertures is in the range of about 2 mm$^2$ to about 12 mm$^2$, according to the 2D X-Ray CT Scan Test herein. At least some of the apertures have a central major axis dimension and a central minor axis dimension, wherein the central major axis dimension is greater than 1.5 mm, when measured at the garment-facing opening area, according to the 2D X-Ray CT Scan Test herein.

In accordance with yet another aspect of the present disclosure, a method is provided for forming a plurality of apertures in a nonwoven substrate for an absorbent article, the substrate defining a first surface and a second surface. A plurality of conical-shaped pins is inserted through the substrate from the first surface to the second surface to form a plurality of corresponding apertures in the substrate. Each of at least a portion of the pins comprises: a first section having a first wall extending from a base portion of the first section to a distal portion of the first section, at least a portion of the first wall disposed at a first angle, the first angle being greater than about 17.5 degrees, greater than about 20 degrees, or greater than about 25 degrees; and a second section having a second wall extending from a base portion of the second section, at least a portion of the second wall disposed at a second angle, the second angle being less than about 20 degrees, less than about 18 degrees, or less than about 16 degrees. The pins are withdrawn from the topsheet, wherein each of at least some of the apertures define: a wearer-facing open area at the wearer-facing surface of the topsheet, the wearer-facing open area is in the range of about 2 mm$^2$ to about 12 mm$^2$, according to the 2D X-Ray CT Scan Test herein; a garment-facing open area at the garment-facing surface of the topsheet, the garment-facing open area is smaller than the wearer-facing open area and in the range of about 1.0 mm$^2$ to about 7.5 mm$^2$, according to the 2D X-Ray CT Scan Test herein, and a side wall, at least a portion of the side wall has an angle in the range of about 55 degrees to about 90 degrees, in the range of about 60 degrees to about 80 degrees, or in the range of about 63 degrees to about 75 degrees, according to the 2D X-Ray CT Scan Test herein.

In accordance with an additional aspect of the present disclosure, a method is provided for forming a plurality of apertures in a nonwoven, liquid permeable substrate for an absorbent article, the substrate defining first and second surfaces. A nonwoven, liquid permeable substrate and a forming apparatus are provided, the forming apparatus comprising a plurality of conical-shaped pins. Each of at least a portion of the pins comprising: a first section having a first wall extending from a base portion of the first section to a distal portion of the first section, at least a portion of the first wall disposed at a first angle, the first angle being greater than about 17.5 degrees, greater than about 20 degrees, or greater than about 25 degrees; and a second section having a second wall extending from a base portion of the second section, at least a portion of the second wall disposed at a second angle, the second angle being less than about 20 degrees, less than about 18 degrees, or less than about 16 degrees. The substrate is conveyed through the forming apparatus, wherein the pins penetrate the substrate and form apertures therein. Each of at least some of the apertures define: a first open area at the first surface of the substrate, the first open area is in the range of about 2 mm$^2$ to about 12 mm$^2$, according to the 2D X-Ray CT Scan Test herein; a second open area at the second surface of the substrate, the second open area is smaller than the first open area and in the range of about 1.0 mm$^2$ to about 7.5 mm$^2$, according to the 2D X-Ray CT Scan Test herein; and a side wall, at least a portion of the side wall has an angle in the range of about 55 degrees to about 90 degrees, in the range of about 60 degrees to about 80 degrees, or in the range of about 63 degrees to about 75 degrees, according to the 2D X-Ray CT Scan Test herein.

In accordance with a further aspect of the present disclosure, a forming apparatus for forming a plurality of apertures in a nonwoven, liquid permeable substrate for an absorbent article is provided, the apparatus comprising: intermeshing members comprising a first member and a second member. The first member comprises a body portion and a plurality of conical-shaped pins. Each of at a least a majority of the pins comprise: a first section having a first wall extending from a base portion of the first section to a distal portion of the first section, at least a portion of the first wall disposed at a first angle, the first angle being greater than about 17.5 degrees, greater than about 20 degrees, or greater than about 25 degrees; and a second section having a second wall extending from a base portion of the second section, the base portion of the second section extending from the first member body portion, at least a portion of the second wall disposed at a second angle, the second angle being different than the first angle and less than about 20 degrees, less than about 18 degrees, or less than about 16 degrees.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

FIG. 24 is a perspective view of a plurality of pins of the apparatus of FIG. 23;

FIG. 27 provides images of a topsheet sample where no external pressure was applied and a topsheet sample where pressure had been applied;

DETAILED DESCRIPTION

Various non-limiting forms of the present disclosure will now be described to provide an overall understanding of the principles of the structure, function, manufacture, and use of the absorbent articles having apertured, three-dimensional materials and method for making the same disclosed herein. One or more examples of these non-limiting forms are illustrated in the accompanying drawings. Those of ordinary skill in the art will understand that the absorbent articles having apertured, three-dimensional materials and method for making the same specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

General Description of an Absorbent Article

Figure 1:
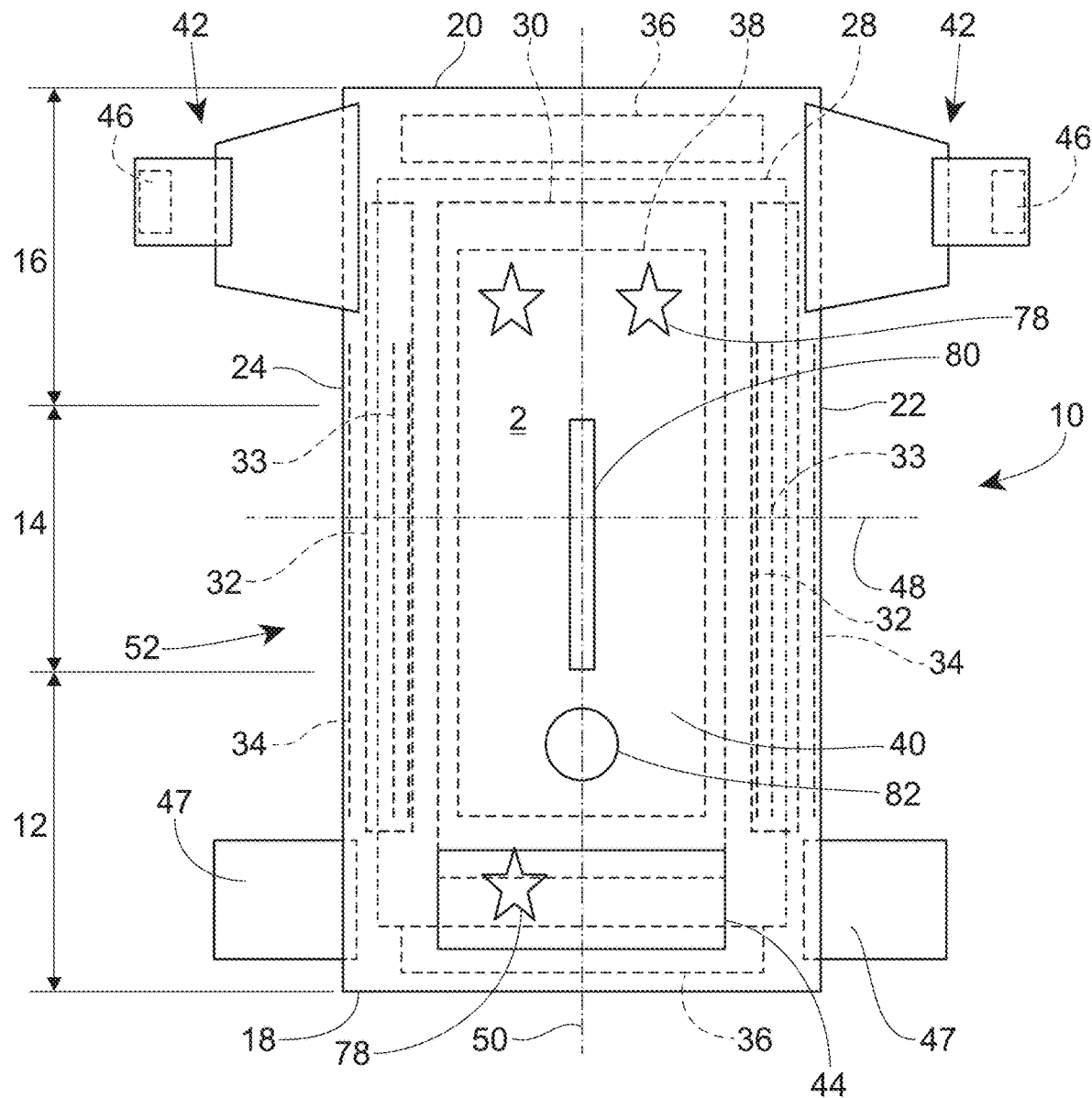
FIG. 1 is a plan view of an example absorbent article in the form of a taped diaper, garment-facing surface facing the viewer, in a flat laid-out state.
Figure 2:
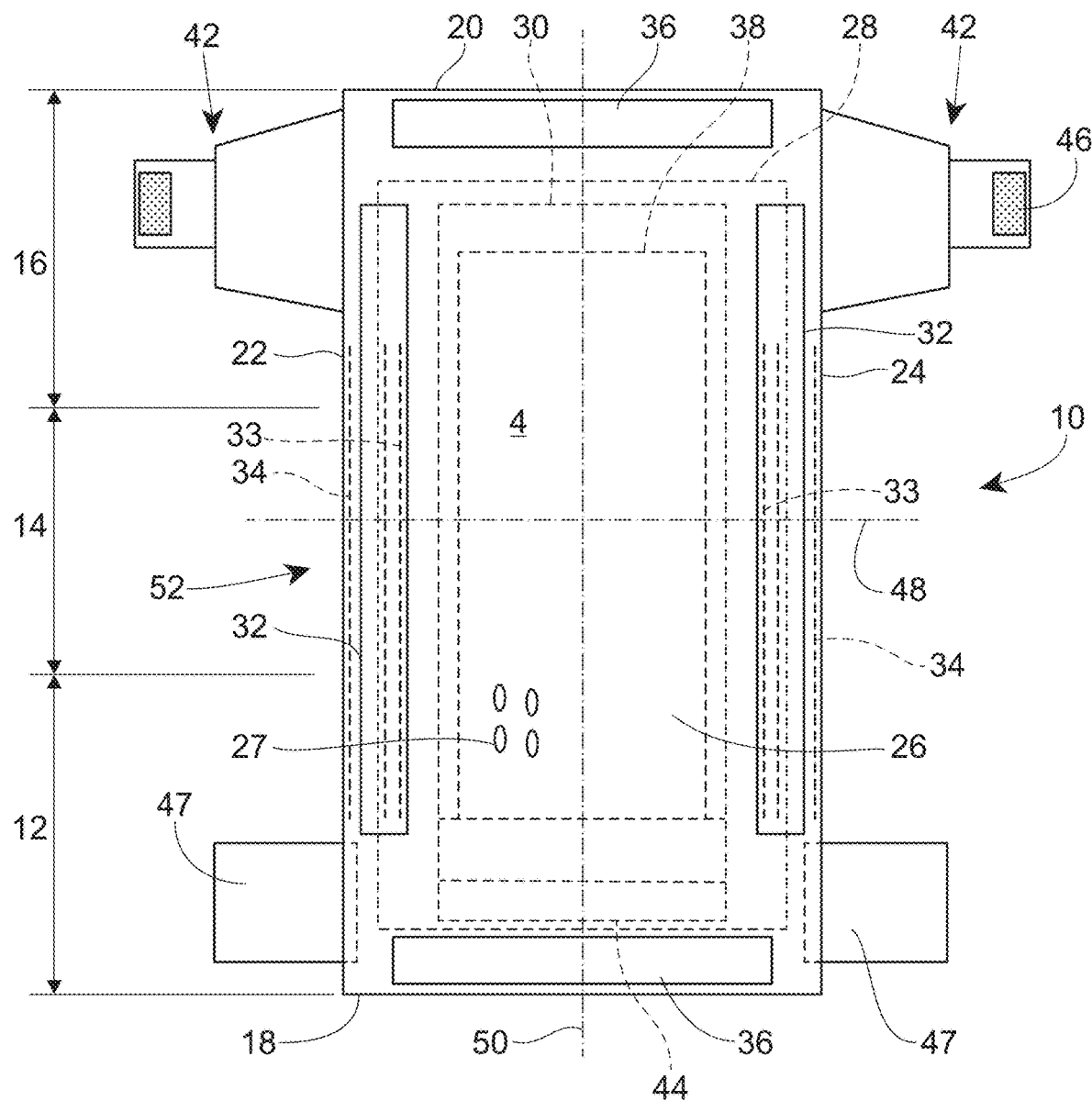
FIG. 2 is a plan view of the example absorbent article of FIG. 1, wearer-facing surface facing the viewer, in a flat laid-out state.
Figure 3:
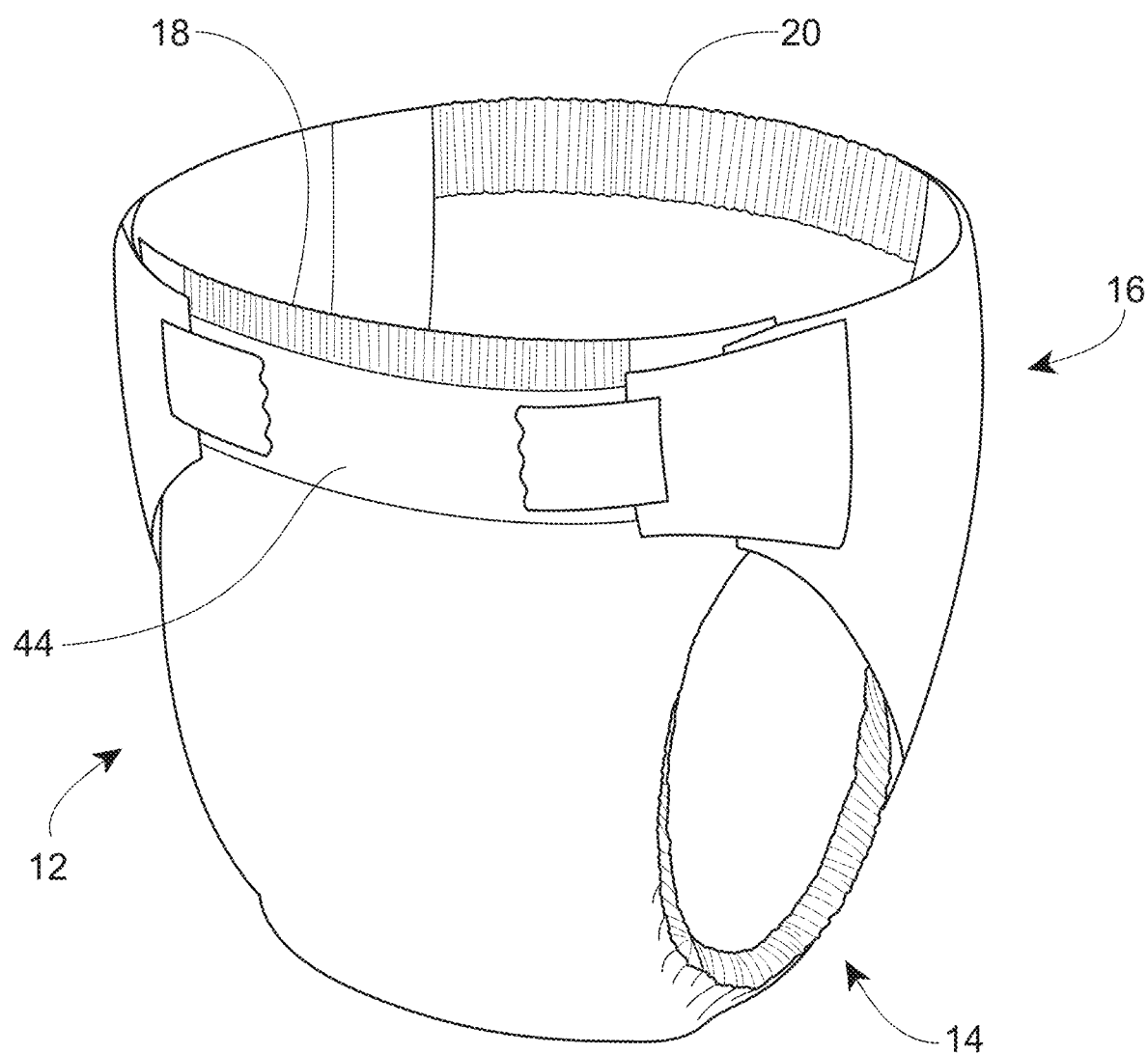
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
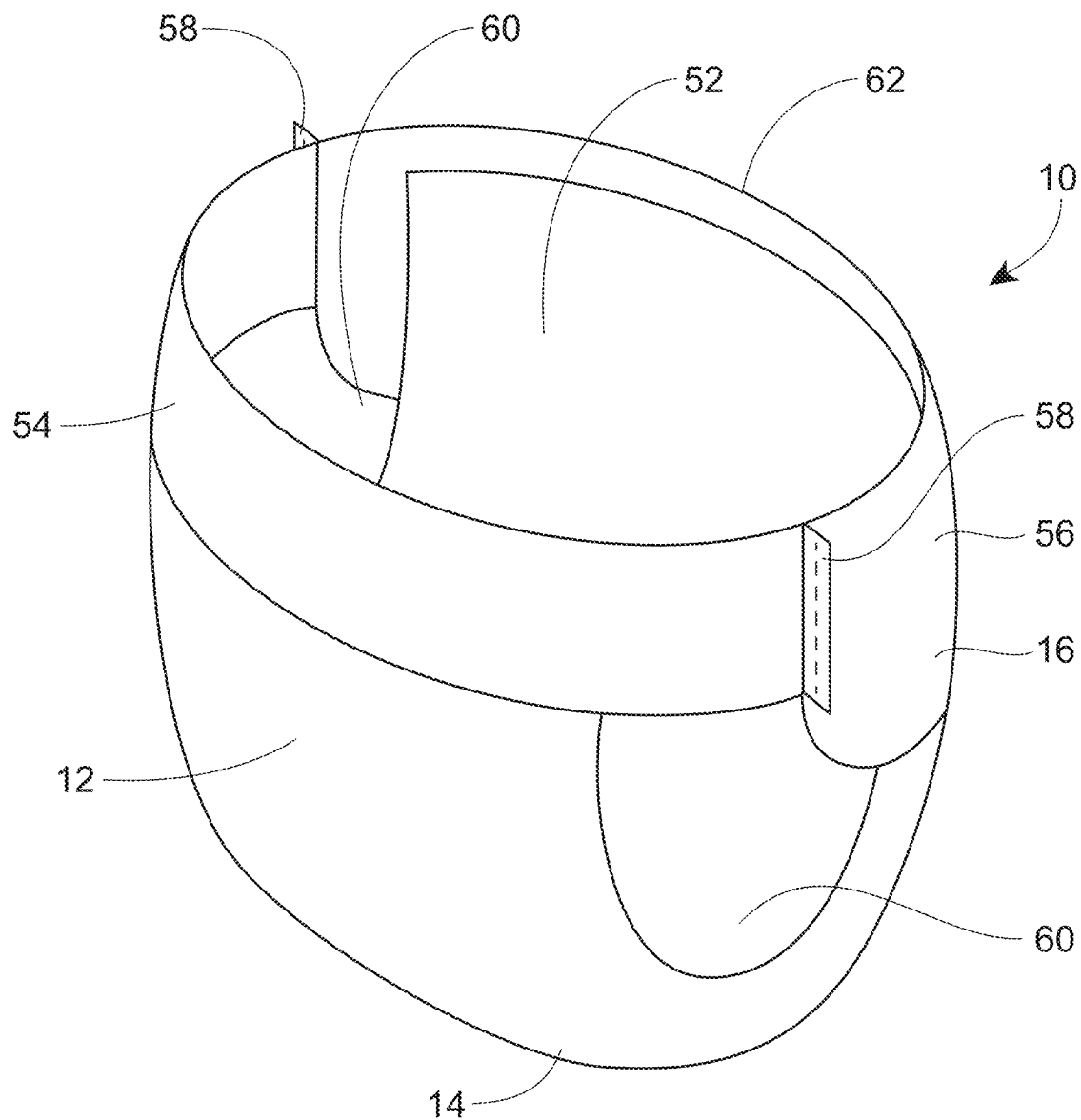
FIG. 4 is a front perspective view of an absorbent article in the form of a pant.
Figure 5:
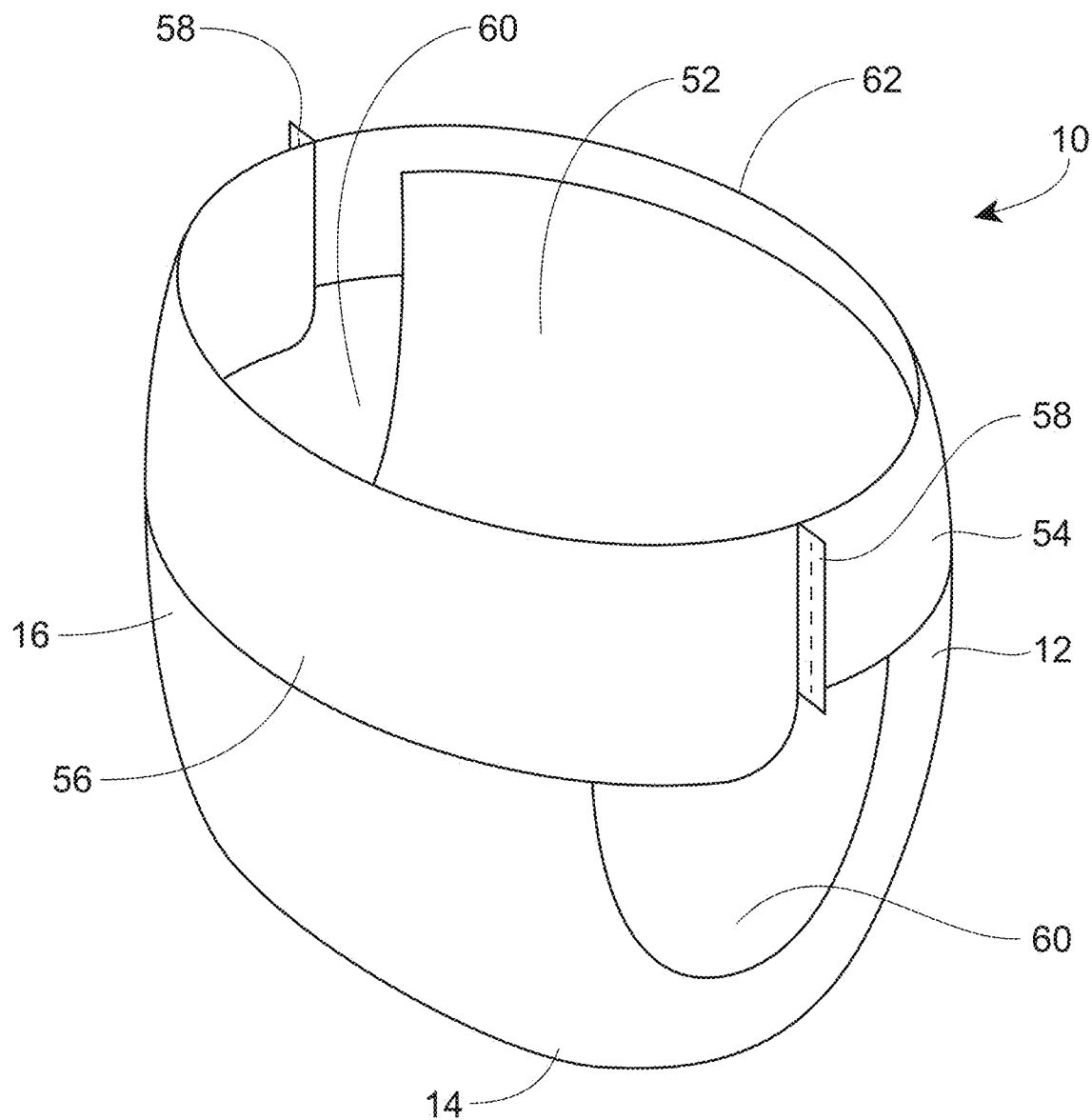
FIG. 5 is a rear perspective view of the absorbent article of FIG. 4.
Figure 6:
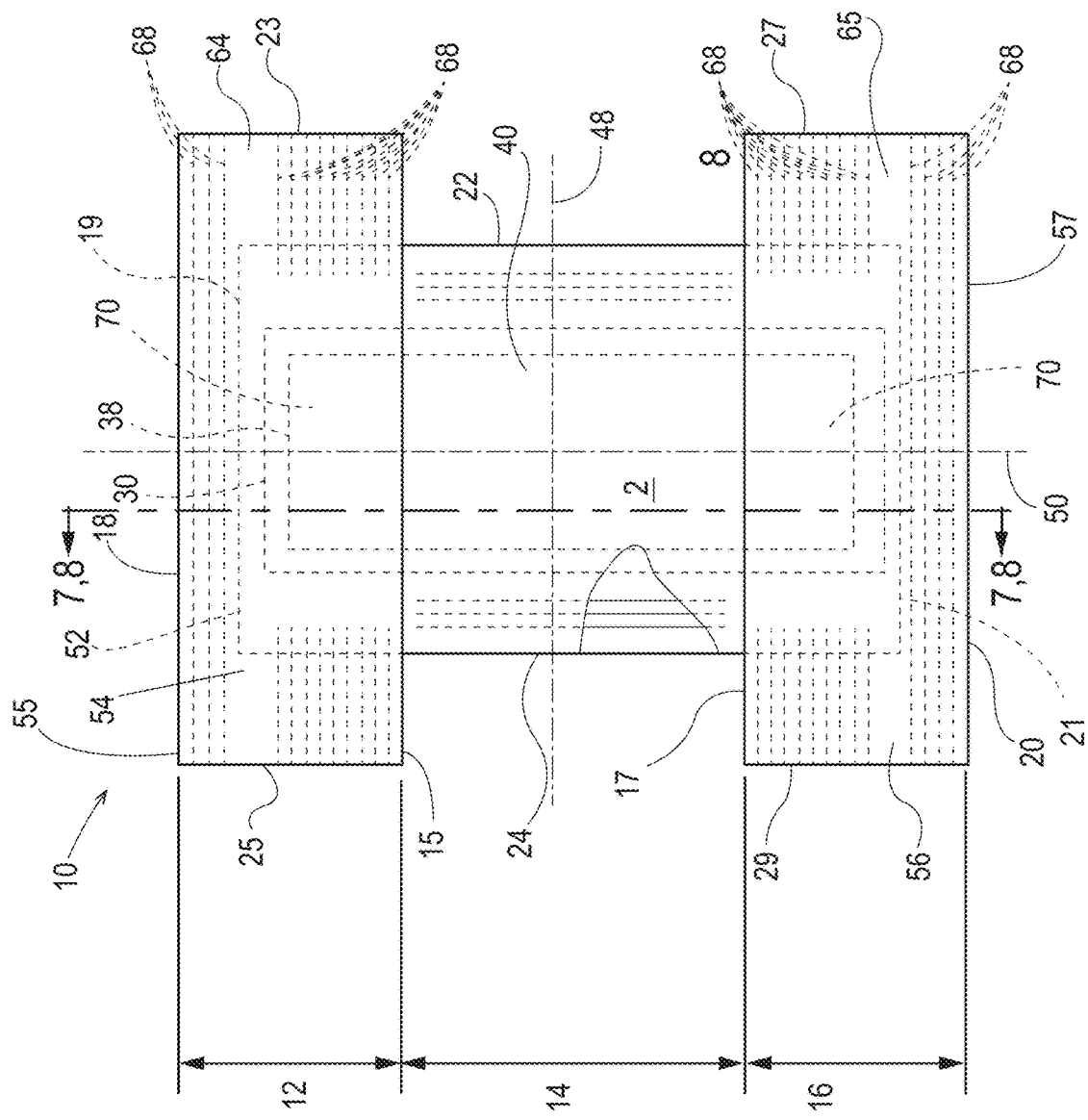
FIG. 6 is a plan view of the absorbent article of FIG. 4, laid flat, with a garment-facing surface facing the viewer.
Figure 7:
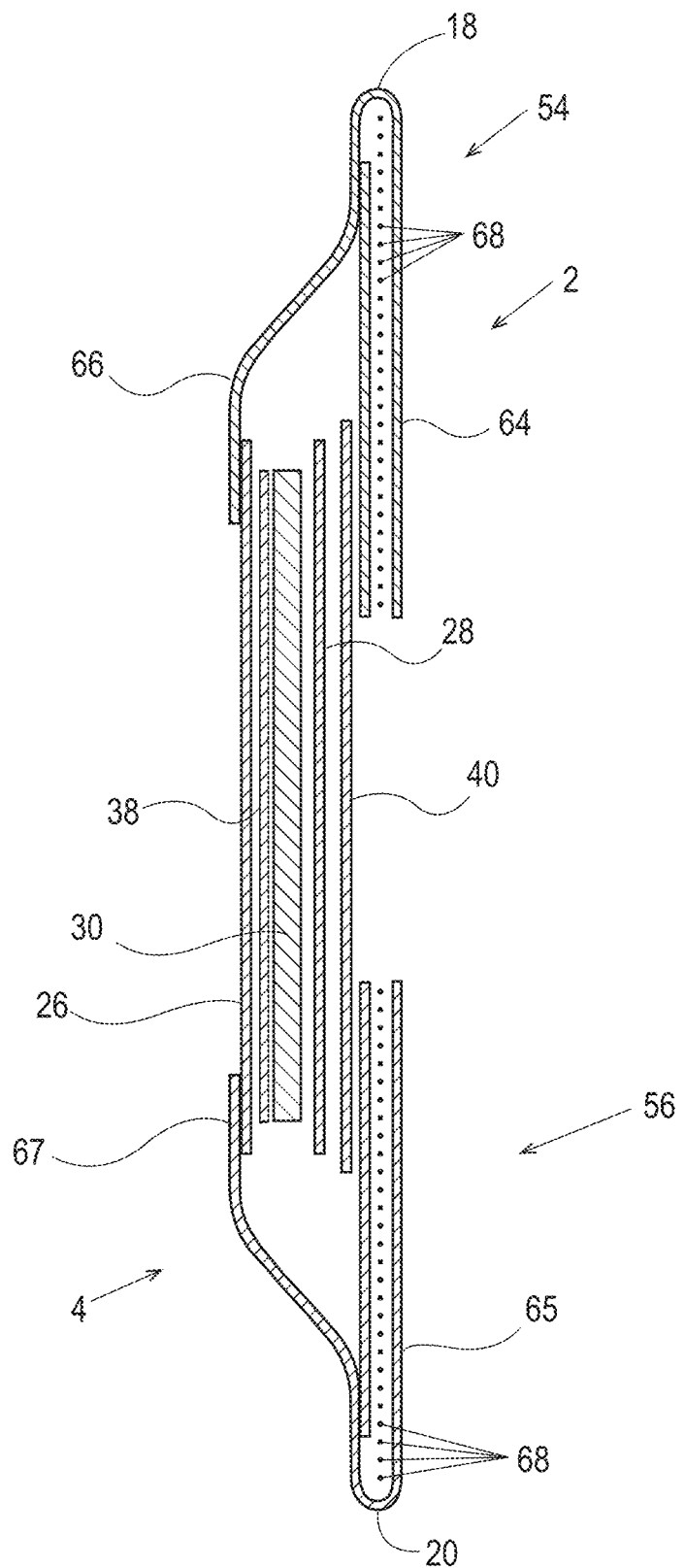
FIG. 7 is a cross-sectional view of the absorbent article taken about line 7-7 of FIG. 6.
Figure 8:
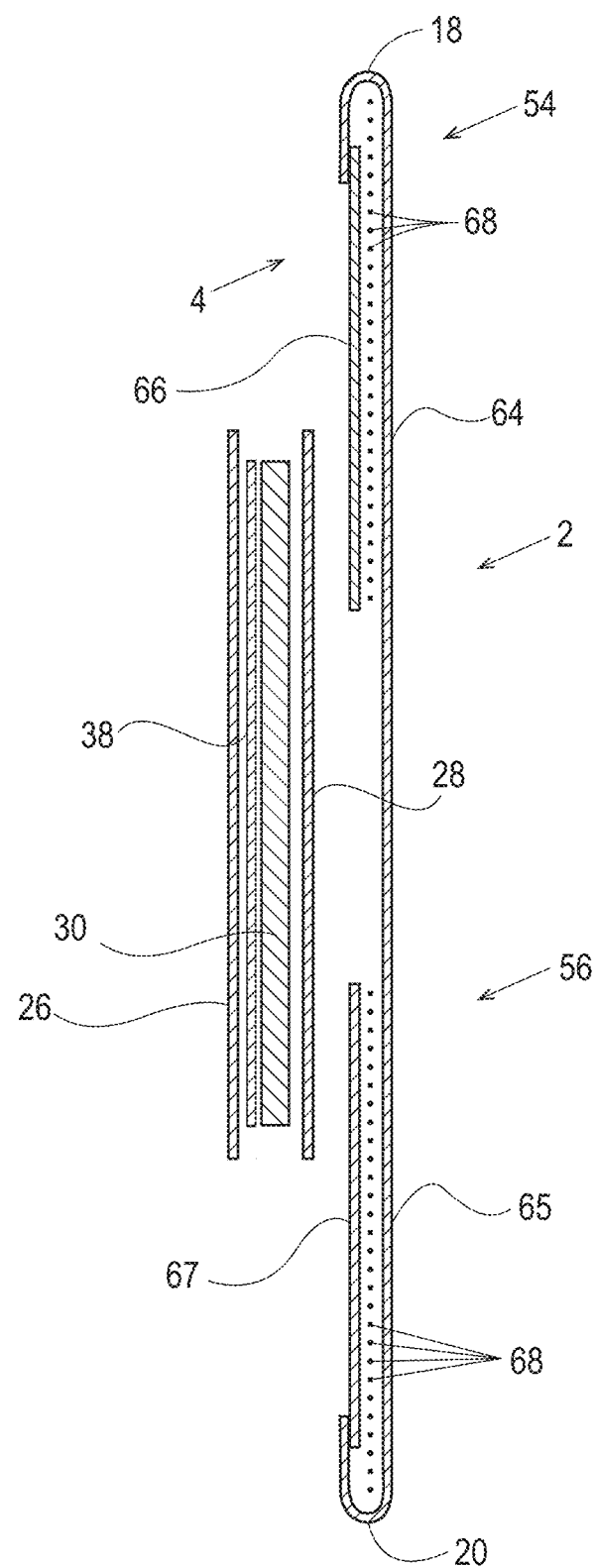
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIG. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIG. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 27), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features.

Absorbent Core

Figure 9:
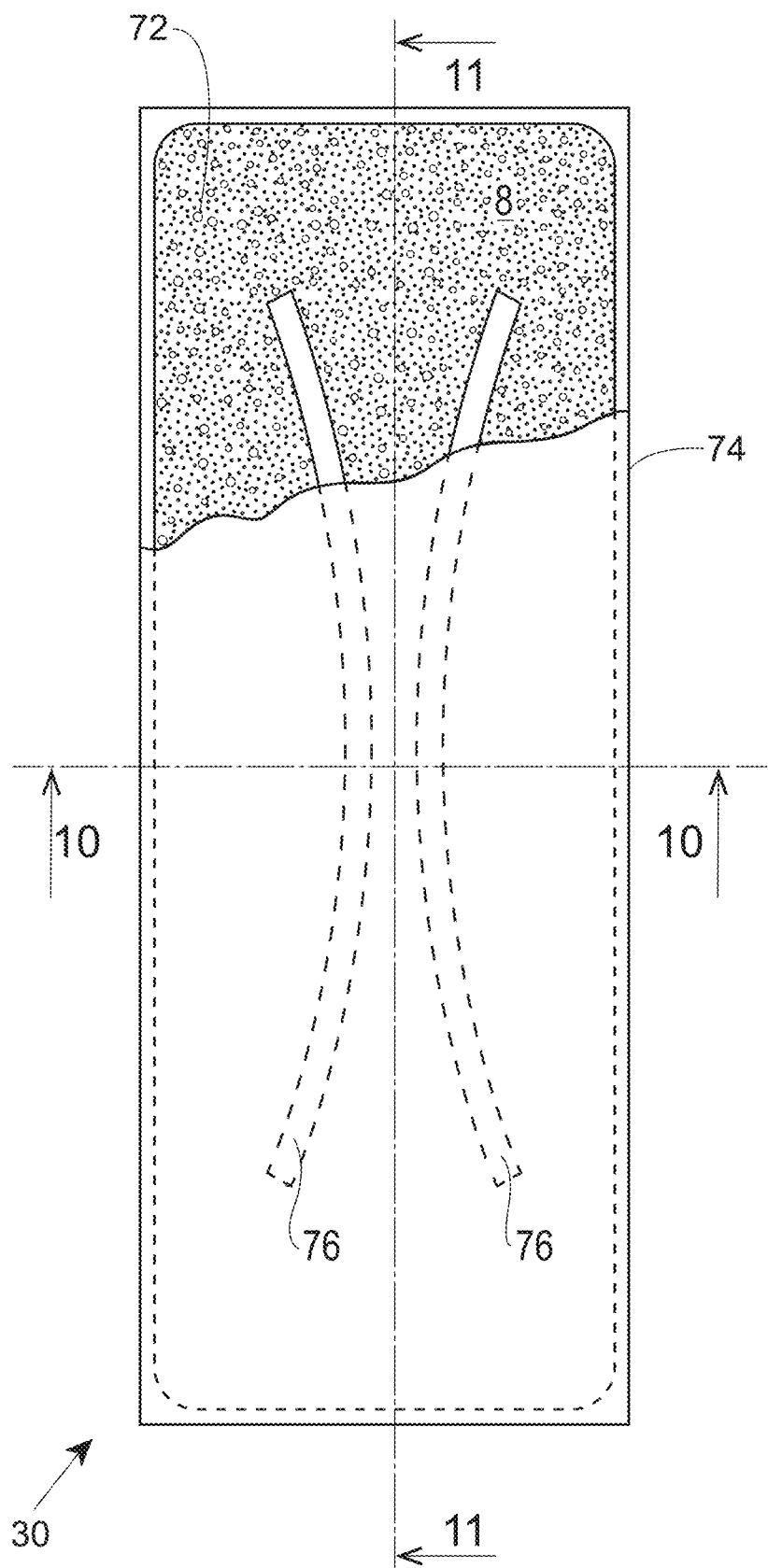
FIG. 9 is a plan view of an example absorbent core or an absorbent article.
Figures 10, 11:
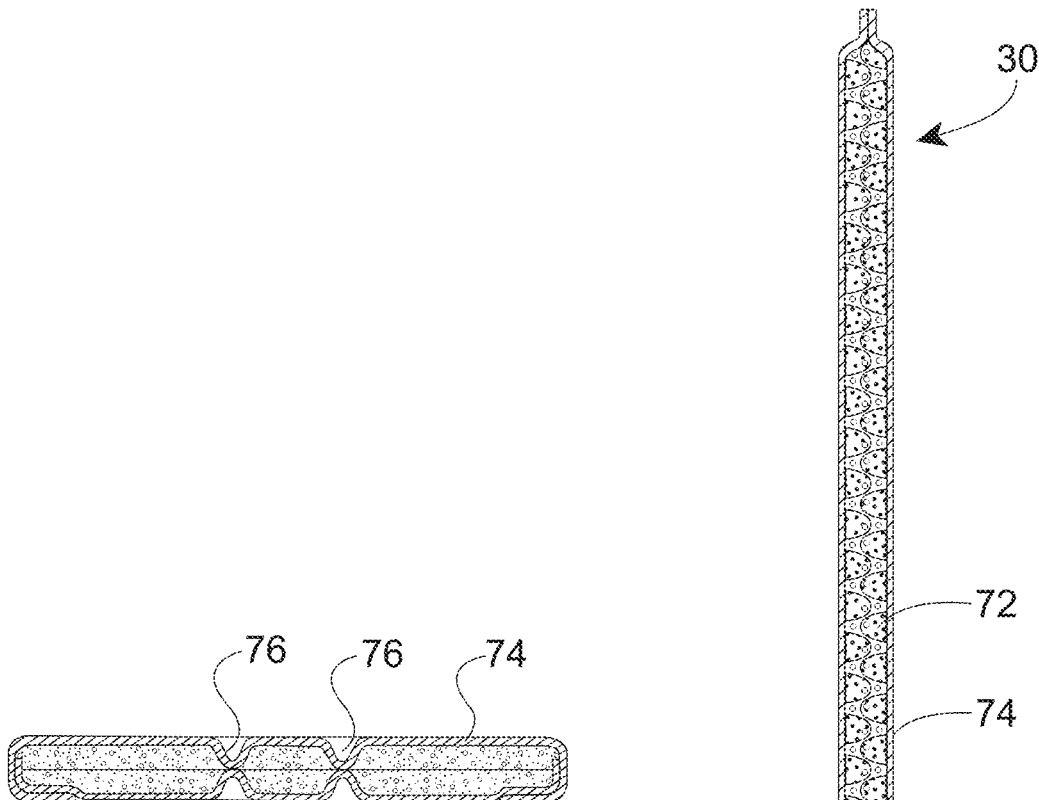
FIG. 10 is a cross-sectional view, taken about line 10-10, of the absorbent core of FIG. 9.
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that providing significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portion of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic stands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Sanitary Napkin

Figure 12:
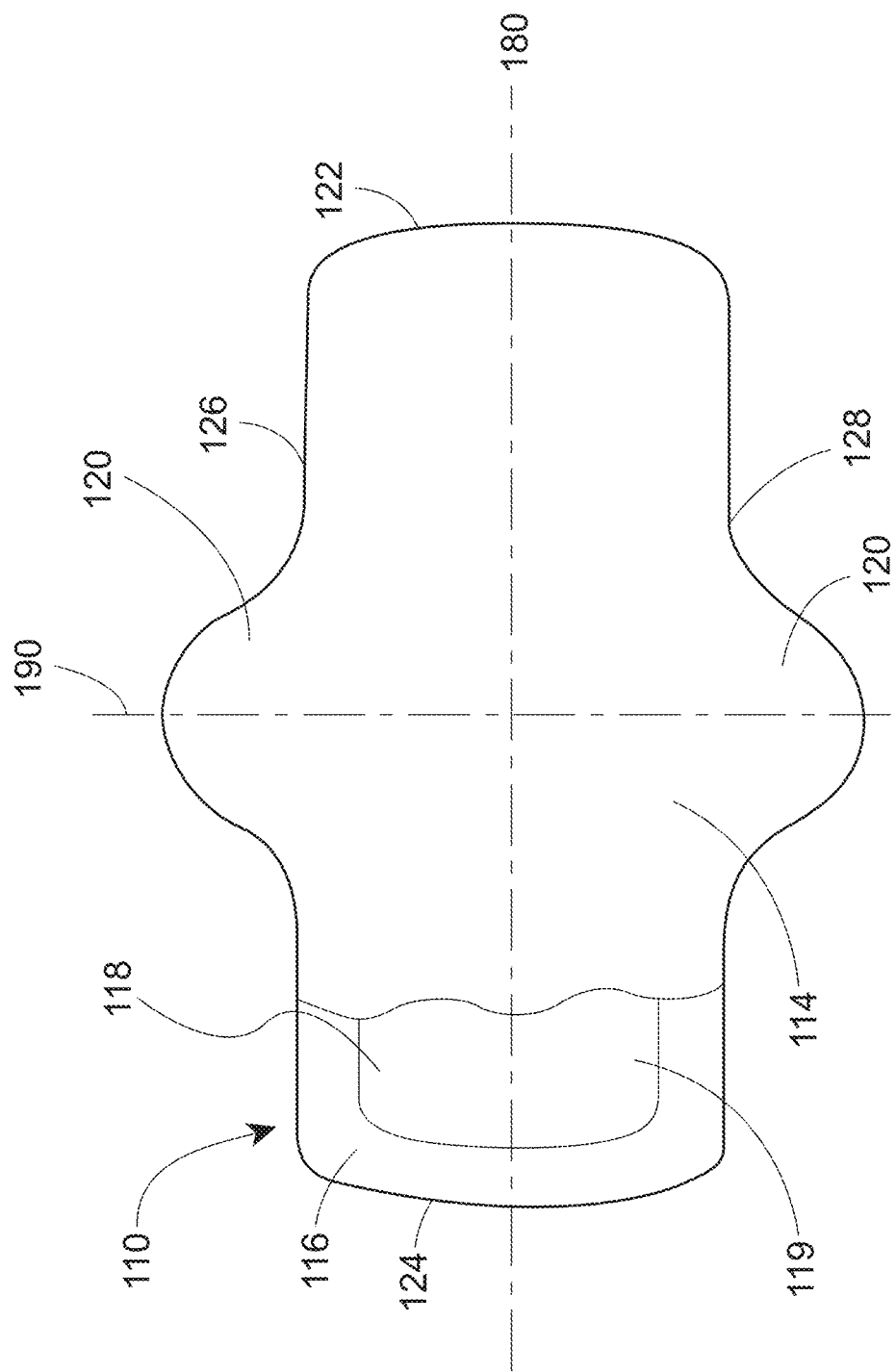
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

Examples Cross-Sections of Absorbent Articles

Figure 13:
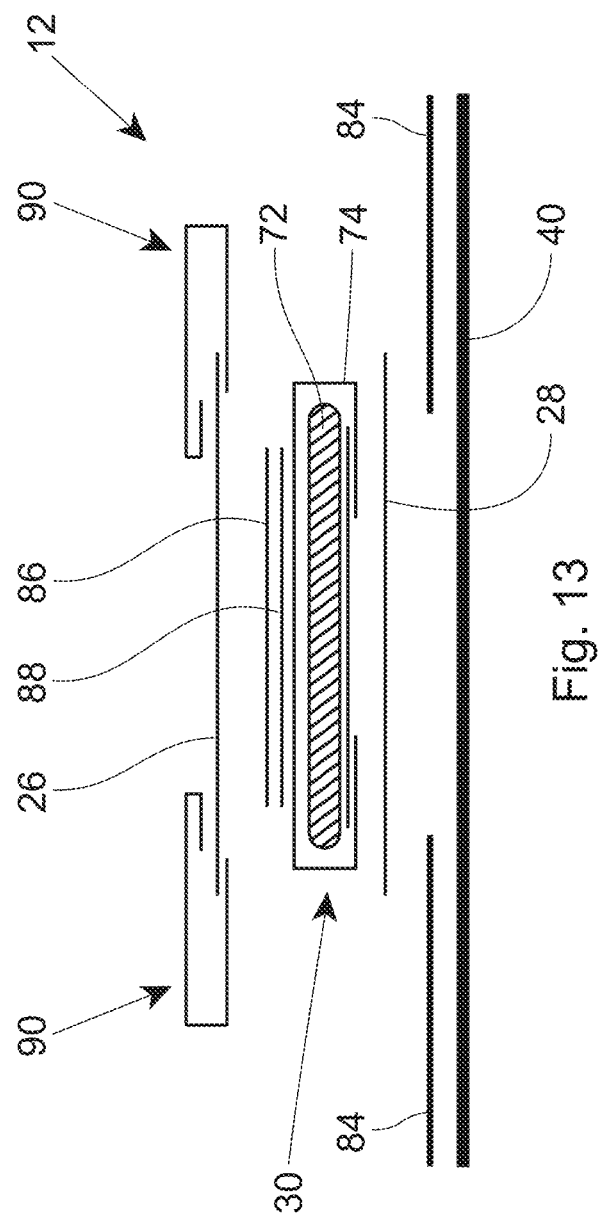
FIG. 13 is an example cross-sectional view taken within a front waist region of an absorbent article.
Figure 14:
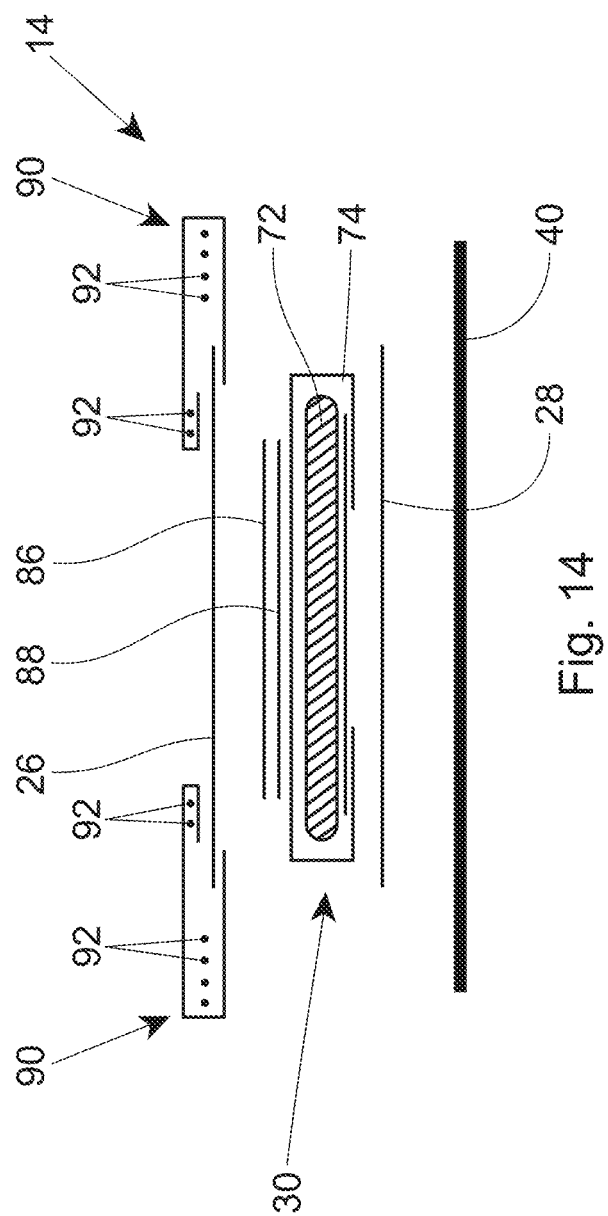
FIG. 14 is an example cross-sectional view taken within a crotch region of an absorbent article.
Figure 15:
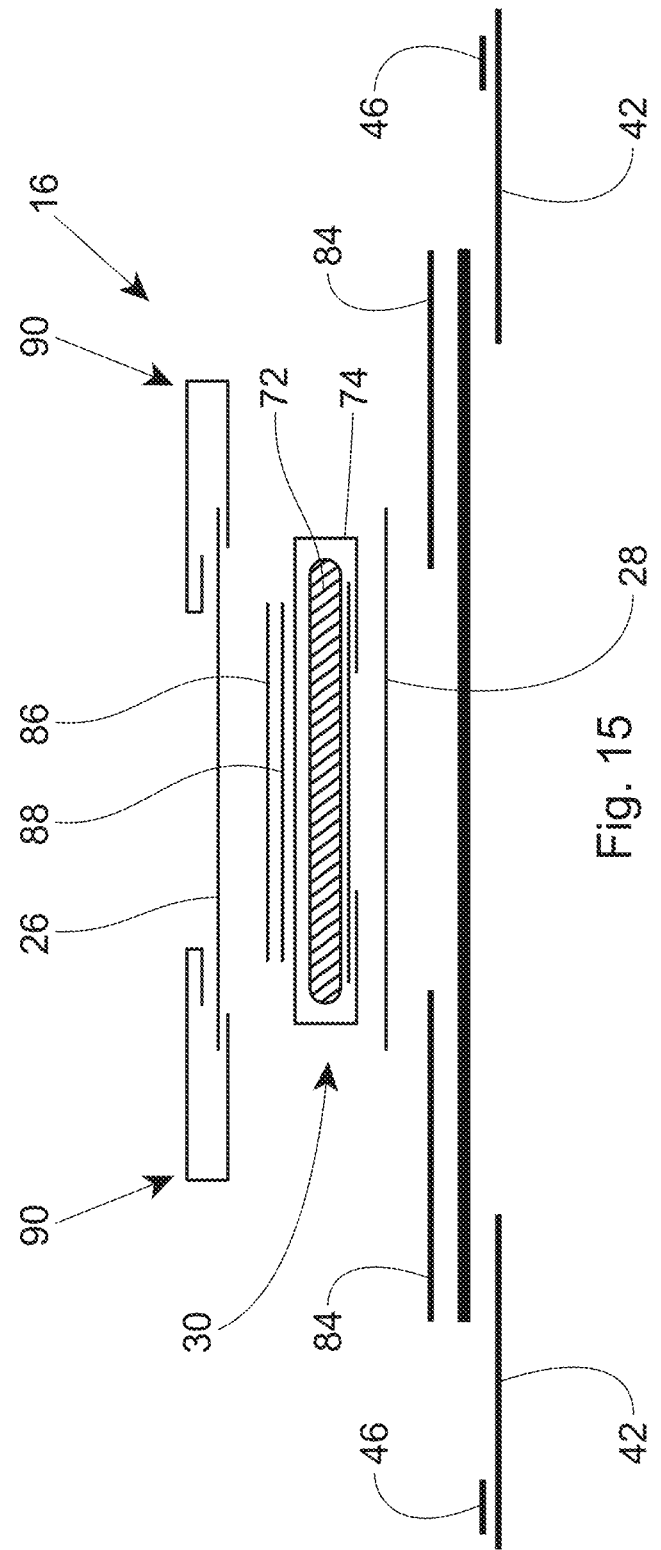
FIG. 15 is an example cross-sectional view taken within a back waist region of an absorbent article.

FIGS. 13-15 illustrate example cross-sectional views of absorbent articles within the scope of the present disclosure. FIG. 13 is an example cross-sectional view taken within a front waist region 12 of an absorbent article. FIG. 14 is an example cross-sectional view taken within a crotch region 14 of an absorbent article. FIG. 15 is an example cross-sectional view taken within a back waist region 16 of an absorbent article. In FIGS. 13-15, an outer cover material is element 40, a liquid permeable topsheet is element 26, opacity patches are elements 84, a liquid impermeable backsheet is element 28, an absorbent core is element 30, with the core bag being element 74, an absorbent material is element 72, and a distribution material is element 86. The distribution material 86 may comprise cross-linked cellulosic material and may be optional. An acquisition material is element 88. A liquid permeable topsheet is element 26. Barrier leg cuffs are elements 90. Elastics in the barrier leg cuffs are elements 92. Back ears are elements 42. Fasteners on the back ears 42 are elements 46. Construction glues and/or bonds between the various layers and/or components have been removed for clarity. Other cross-sectional configurations known to those of skill in the art are also within the scope of the present disclosure.

General Structure and Properties of a Substrate

Figure 16:
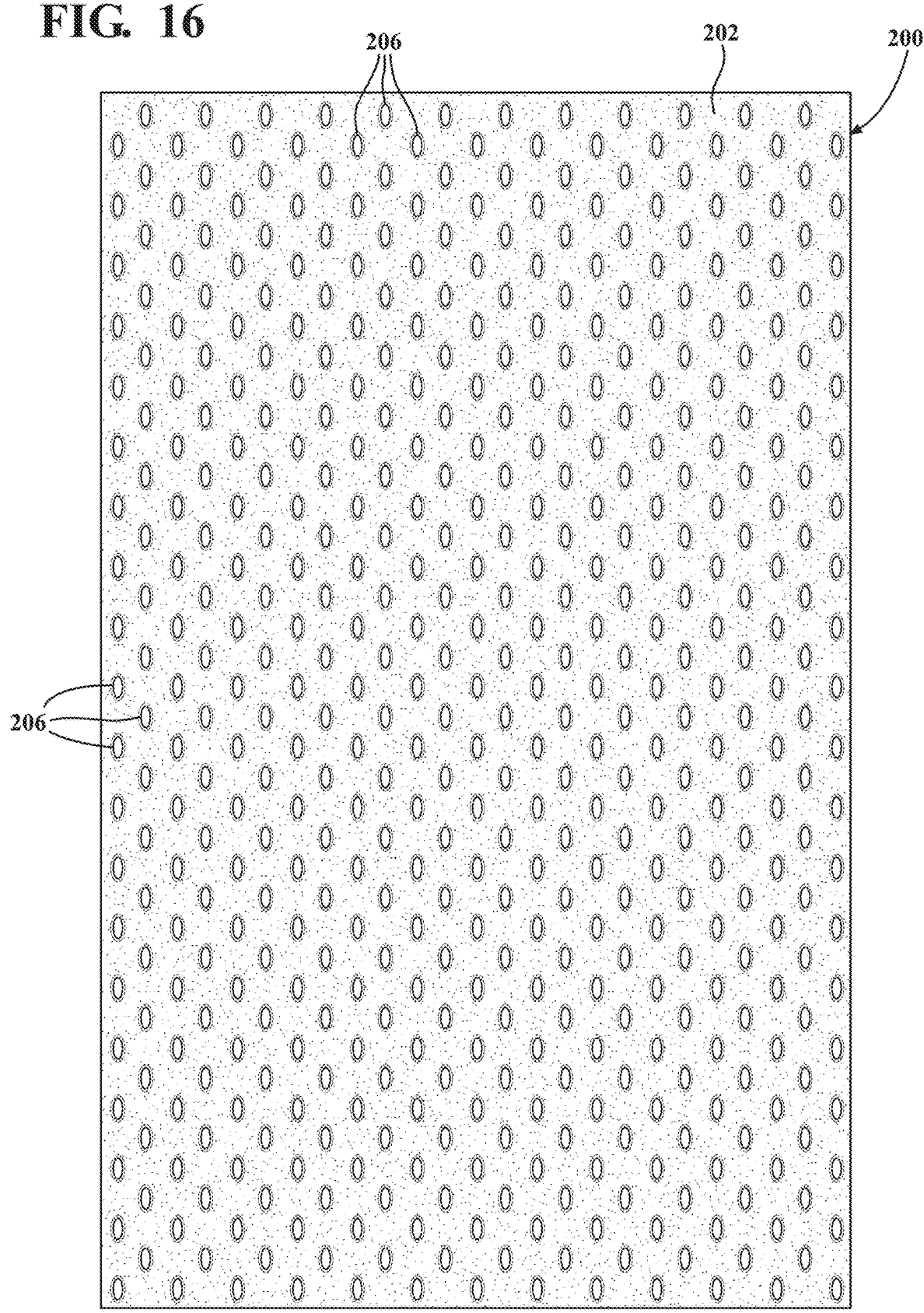
FIG. 16 is a plan view of an example substrate, a wearer-facing surface facing the viewer.

The substrates of the present disclosure may be used as a component of, or portion of a component of, an absorbent article, such as a diaper, a pant, or a sanitary napkin. Some examples of such use may be a topsheet, an outer cover nonwoven, and/or a portion of an ear, for example. Even though a topsheet may be referred to herein as an example, it will be understood that the substrates may be used as any component of an absorbent article. FIG. 16 is a plan view of a portion of an example substrate for absorbent articles according to the present disclosure, such as a topsheet 200, in which a first surface of the topsheet 200 comprising a wearer-facing surface 202 of the topsheet 200 is facing the viewer. A second surface of the topsheet 200 comprising a garment-facing surface 204 is illustrated in FIGS. 17 and 18, where FIG. 17 is a cross-sectional view of the topsheet 200 taken along view line 17-17 in FIG. 16A before compressive forces $F_C$ are applied to the topsheet 200, and FIG. 18 is a cross-sectional view of the topsheet 200 taken along view line 17-17 after compressive forces $F_C$ are applied to the topsheet 200. FIG. 19 is an enlarged view of a plurality of apertures 206 formed in the topsheet 200. The topsheet 200 illustrated in FIGS. 16-19 (excluding FIG. 17A, which shows a related art aperture) and described herein may form a part of any of the absorbent articles described herein, or may be used in other types of absorbent articles as will be appreciated by those having ordinary skill in the art.

The topsheet 200 may be formed from any suitable nonwoven materials and comprises a single layer or multiple layers, e.g., two or more layers. If multiple layers are used, they may be comprised of the same type of nonwoven materials, or different types of nonwoven materials. In some cases, the topsheet 200 may be free of a film. A thickness T of the topsheet 200 may be in the range of about 0.2 mm to about 3 mm, in the range of about 0.5 mm to about 2 mm, or in the range of about 0.7 mm to about 1.5 mm, see FIG. 17.

The topsheet 200 may comprise a layer of fibers, such as hydrophobic fibers. The layer of fibers may be made of any suitable materials including, but not limited to natural materials, synthetic materials, and combinations thereof. Suitable natural materials may comprise, but are not limited to cellulose, cotton linters, bagasse, wool fibers, silk fibers, etc. Cellulose fibers may be provided in any suitable form, comprising but not limited to individual fibers, fluff pulp, drylap, liner board, etc. Suitable synthetic materials may comprise, but are not limited to nylon, rayon and polymeric materials. Suitable polymeric materials may comprise, but are not limited to: polyethylene (PE), polyester, polyethylene terephthalate (PET), polypropylene (PP), polylactic acid (PLA), and co-polyester. In some forms, however, the topsheet 200 may be either substantially, or completely free, of one or more of these materials. For example, in some forms, the topsheet 200 may be substantially free of cellulose, and/or exclude paper materials. In some forms, one or more layers of the topsheet 200 may comprise up to 100% thermoplastic fibers. The fibers in some cases may, therefore, be substantially non-absorbent. The layer of fibers may be 100% carded fibers, 100% spunbond fibers, or one or more layers of carded fibers and one or more layers of spunbond fibers. One or more layers of the topsheet 200 may comprise cotton fibers. At least some of the fibers may comprise bicomponent fibers including a core and a sheath. The core may comprise polyethylene terephthalate (PET) and the sheath may comprise polyethylene (PE). Alternatively, the core may comprise polypropylene (PP) or polylactic acid (PLA). The fiber may be comprised of about 30% to about 60% core (e.g., PET), about 70% to about 40% sheath (e.g., PE), and optionally up to about 4% Titanium dioxide (TiO2), i.e., 0% to about 4% TiO2. According to one example, the PET and PP portions may each make up about 49% of the composition of the fiber, e.g., PET and PE making up about 98% of the composition of the fiber, with the other 2% being TiO2.

Moreover, at least some of the fibers may have a denier per filament of about 1 to about 3, about 1.5 to about 2.5, or about 2.

The basis weight of nonwoven materials is usually expressed in grams per square meter (gsm). The basis weight of a single layer nonwoven material may range from about 8 gsm to about 100 gsm, depending on the ultimate use of the material. For example, the topsheet 200 may have a basis weight from about 10 gsm to about 35 gsm, about 15 gsm to about 30 gsm, about 18 gsm to about 25 gsm, or about 20 gsm to about 24 gsm. All basis weights are calculated according to the Basis Weight Test herein.

Apertures Formed Through the Topsheet

Figure 16A:
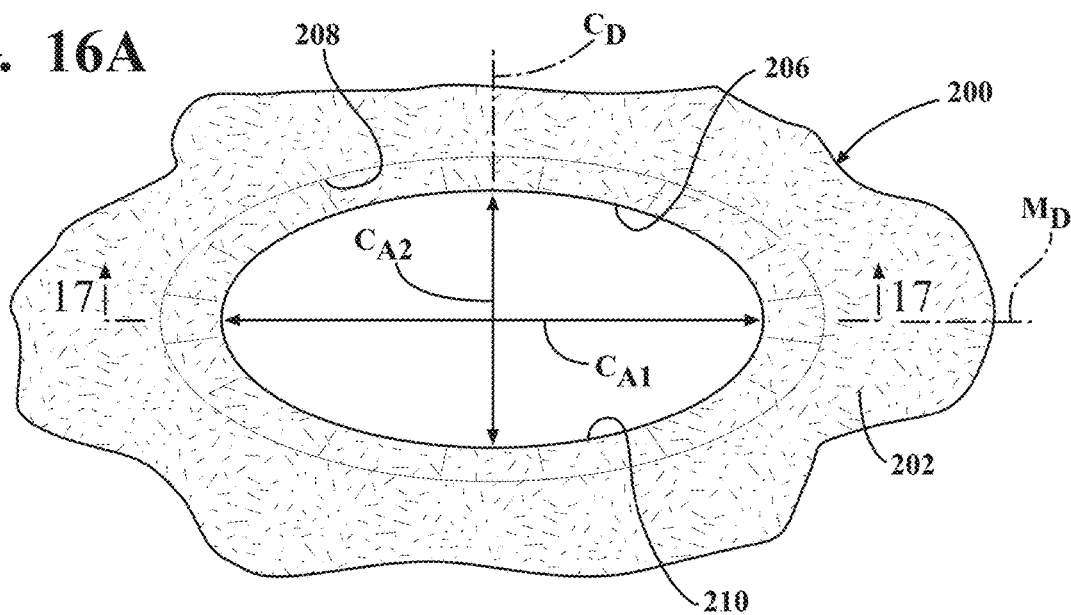
FIG. 16A is an enlarged view of an aperture formed in the substrate of FIG. 16.
Figure 17:
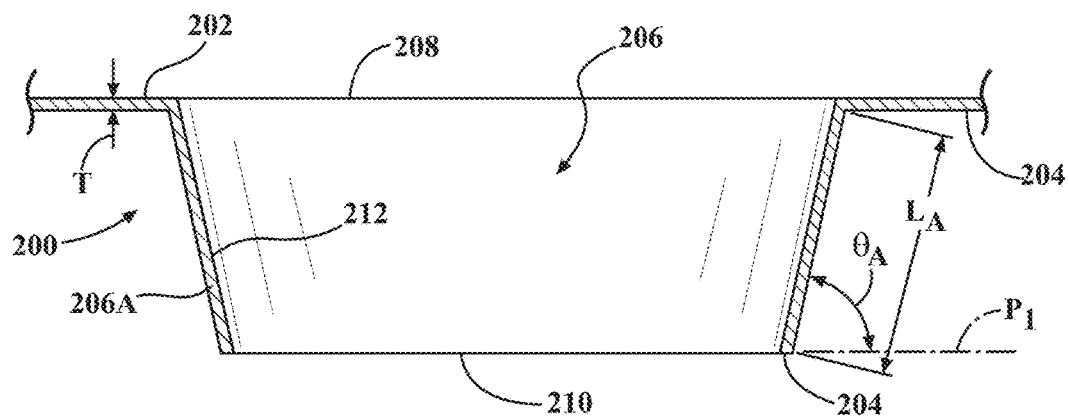
FIG. 17 is a cross sectional view taken along line 17-17 of FIG. 16A.

An example aperture 206, as illustrated in FIG. 16A, formed though the layer of fibers of the topsheet 200 will now be described. It is understood that the topsheet 200 may include one or more of the described apertures 206, although not all of the apertures in the topsheet 200 need be as described, i.e., one or more conventional apertures or one or more other types of apertures described herein may also be formed through the topsheet 200.

In the example topsheet 200 depicted in FIGS. 16-19 (including FIG. 16A but excluding FIG. 17A, which shows a related art aperture), the apertures 206 are formed in the topsheet 200 and comprise a wearer-facing opening area 208 at the wearer-facing surface 202 and a garment-facing opening area 210 defined in displaced topsheet material comprising a tail 206A. The apertures 206 allow the passage of liquid bodily exudates, e.g., runny bowel movements, urine, menses, etc., through the topsheet 200 and thus make the topsheet 200 a liquid permeable substrate, even though the fibers of the topsheet 200 may be hydrophobic. As shown in FIGS. 16A, 17 and 18, the wearer-facing opening area 208 is larger than the garment-facing opening area 210, where the wearer and garment-facing opening areas 208, 210 are measured according to the 2D X-Ray CT Scan Test herein. The wearer-facing opening area 208 of the aperture 206 is in the range of about 2 mm² to about 12 mm², or in the range of about 3 mm² to about 8 mm². The garment-facing opening area 210 of the aperture 206 is in the range of about 1.0 mm² to about 7.5 mm², or in the range of about 1.7 mm² to about 4 mm².

A side wall 212, defined by the tail 206A, extends from the wearer-facing opening area 208 to the garment-facing opening area 210 and has an inward taper. In the example shown, the taper of the side wall 212 is continuous from the wearer-facing opening area 208 to the garment-facing opening area 204, but could be discontinuous therebetween without departing from the scope and spirit of the present disclosure. In accordance with the present disclosure and as shown in FIG. 17, the side wall 212 is disposed at an angle $\theta_A$ measured with respect to a plane $P_1$ generally parallel to the wearer-facing surface 202. The angle $\theta_A$ may be greater than 55 degrees, in the range of about 55 degrees to about 90 degrees, in the range of about 60 degrees to about 80 degrees, or in the range of about 63 degrees to about 75 degrees.

In accordance with the present disclosure, the angle $\theta_A$ is defined such that the side wall 212 extends from the wearer-facing opening area 208 to the garment-facing opening area 210 at a steep angle, e.g., the angle $\theta_A$ measured with respect to a plane $P_1$ generally parallel to the wearer-facing surface 202 may be in the range of about 55 degrees to about 90 degrees, in the range of about 60 degrees to about 80 degrees, or in the range of about 63 degrees to about 75 degrees. It is believed that in the related art, the angle defined by a side wall extending from a wearer-facing opening area 208 to the garment-facing opening area 210 was less steep. By forming the side wall 212 with a steep angle, two advantages are believed to result. First, a smaller wearer-facing opening area 208 may be used, causing less skin markings on the user, yet yield a similar bodily fluid flow rate through the aperture 206 to that of a related art aperture having a substantially larger wearer-facing opening area 208 and a similar sized garment-facing opening area 210. Also, a larger wearer-facing opening area results in a longer tail or side wall, which is more likely to deform inwardly toward the aperture center and limit or block flow through the aperture. Smaller wearer-facing opening areas are easy to form with very steep angles as the pins for forming apertures with smaller wearer-facing opening areas are shorter in length. Second, as will be discussed further below, it is believed that when the side wall 212 is steep, it is unlikely to fold back into the aperture 206 so as to partially or substantially fully close the aperture 206.

In the illustrated form, the apertures 206 have a generally ellipse-like shape, see the aperture 206 illustrated in FIG. 16A. As shown in FIG. 16A, the ellipse-like shaped aperture 206 has a central major axis dimension $C_{A1}$ and a central minor axis dimension $C_{A2}$, which, in the illustrated form, are measured at the garment-facing opening area 210. The central minor axis dimension $C_{A2}$ has a length from one side of the aperture 206 to the opposing side that is shorter than that of the central major axis dimension $C_{A1}$. In one example, the central major axis dimension $C_{A1}$ is greater than 1.5 mm and in the range of about 1.5 mm to about 3.5 mm, in the range of about 2 mm to about 3 mm, or in the range of about 2.2 mm to about 2.8 mm, when measured at the garment-facing opening area 210. In one example, the central minor axis dimension $C_{A2}$ is greater than 0.5 mm and in the range of about 0.5 mm to about 2.5 mm, in the range of about 0.9 mm to about 1.5 mm, or in the range of about 1 mm to about 1.4 mm, when measured at the garment-facing opening area 210. A ratio of the central major axis dimension $C_{A1}$ to the central minor axis dimension $C_{A2}$ may be at least 1.3, but less than 4, or at least 1.5, but less than 3.

The apertures 206 may be arranged in the topsheet 200 such that the topsheet 200 has an Effective Open Area in the range of about 15% to about 30%, in the range of about 18% to about 25%, or in the range of about 20% to about 24%, as measured at the garment-facing surface 204, according to the Aperture Test herein. Such an Effective Open Area may be accomplished with a first spacing $S_1$ in a first direction (a side-to-side direction as shown in FIG. 19) between adjacent apertures 206, as measured at the wearer-facing surface 202, of about 3.0 mm and a second spacing $S_2$ in a second direction (an up and down direction as shown in FIG. 19) between adjacent apertures 206, as measured at the wearer-facing surface 202, of about 2.5 mm, where the central major axis dimension $C_{A1}$ of the apertures 206 is about 2.5 mm and the central minor axis dimension $C_{A2}$ of the apertures 206 is about 1.2 mm.

In some aspects, the apertures 206 may all be of a similar size and/or shape, and in other aspects, the apertures 206 may be of one or more different sizes and/or shapes.

With reference now to FIGS. 17 and 18, the effect of compressive forces $F_C$ on the topsheet 200 will now be described, wherein the compressive forces $F_C$ may be exerted to the topsheet 200 including a component in a direction generally perpendicular to the wearer-facing surface 202. Such compressive forces $F_C$ may occur, for example, as a wearer of an absorbent article including the topsheet 200 sits on a surface, such as a chair, floor, etc.

Figure 17A:
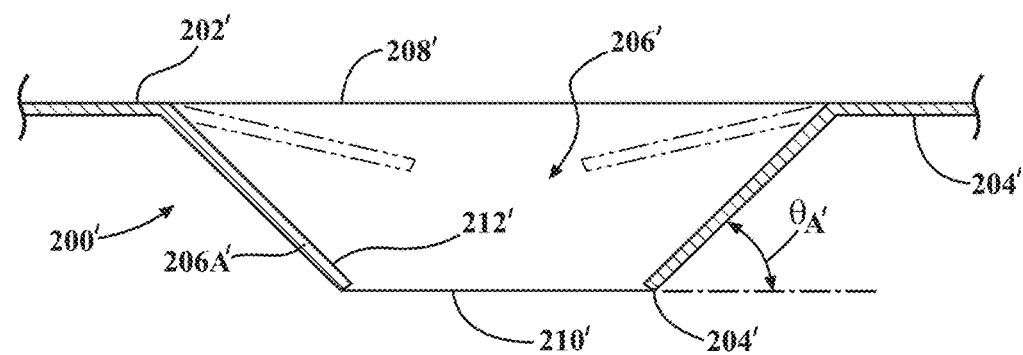
FIG. 17A is a cross sectional view similar to FIG. 17 but of a related art aperture.
Figure 18:
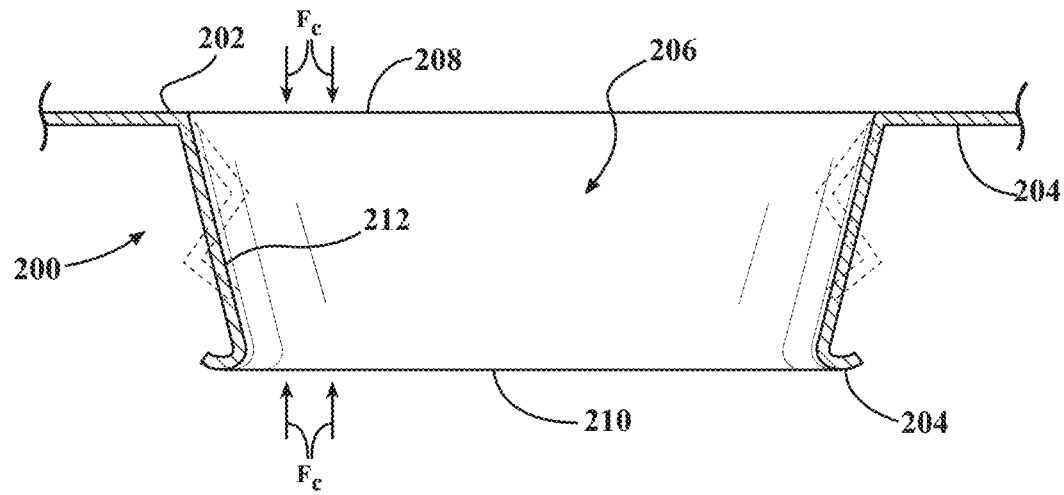
FIG. 18 is a view similar to that of claim 17, but after compressive forces has been applied to the substrate.
Figure 19:
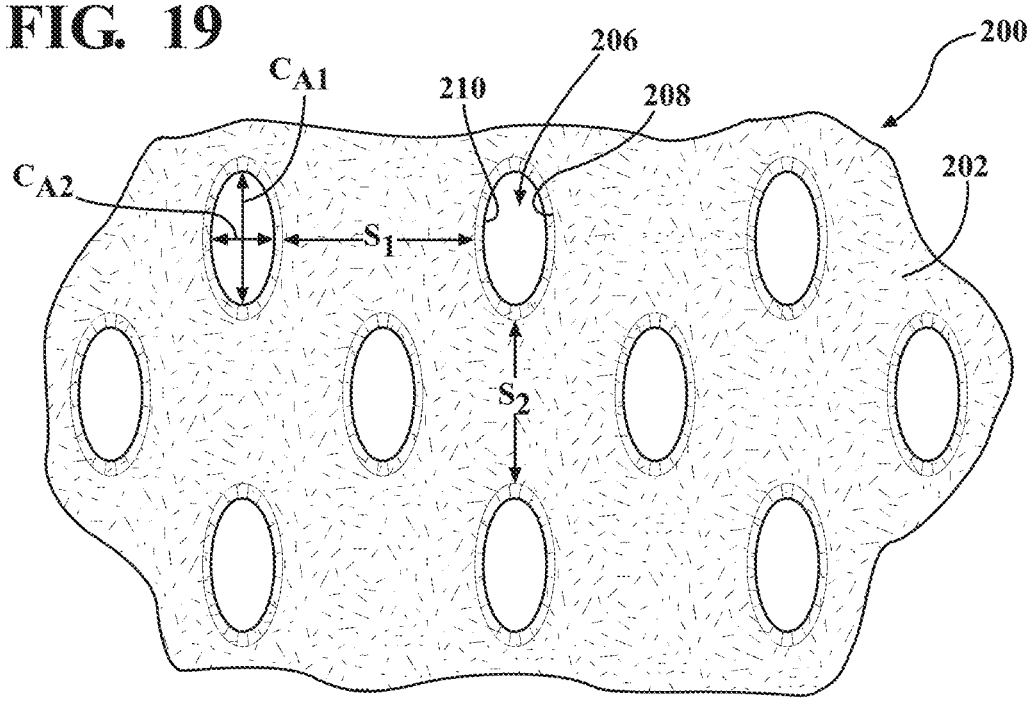
FIG. 19 is an enlarged view showing a plurality of apertures in the substrate of FIG. 16.

As a result of the compressive forces $F_C$ shown in FIG. 18, the side wall 212 of the aperture 206 at the garment-facing open area 210 is believed to fold outwardly, i.e., away from the center of the aperture 206, or to buckle as shown in the phantom lines on the left or right side portions of the side wall in FIG. 18, as opposed to folding inwardly toward the center of the aperture 206, as is the case with the related art aperture 206' illustrated in FIG. 17A (in FIG. 17A, structure corresponding to that shown in FIGS. 17 and 18 includes the same reference numeral followed by a prime symbol). Since the side wall 212 of the aperture 206 shown in FIG. 18 folds outwardly at the garment-facing open area 210 or buckles generally along its own axis, the garment-facing opening area 210 of the aperture 206 is not reduced (or is reduced only very slightly) as a result of the compressive forces $F_C$, thus avoiding (or minimizing) a decrease in the amount of fluid able to flow through the aperture 206 when the topsheet 206 is experiencing or has experienced compressive forces $F_C$. This is in contrast to the situation of FIG. 17A, where the side wall 212' of the aperture 206' at the garment-facing open area 210' folds inwardly as shown in phantom, since the side wall 212' has a less steep angle $\theta_A'$, which inward folding of the side wall 212' at the garment-facing open area 210' may cause a decrease in the garment-facing opening area 210' of the aperture 206'. Such a decrease would reduce the amount of fluid able to flow through the aperture 206' when the topsheet 200' is experiencing or has experienced compressive forces $F_C$.

When an ellipse-like shaped aperture 206 is formed, topsheet material is displaced inwardly, i.e., in a direction away from the wearer-facing surface 202, thereby forming the side wall 212. The side wall 212 has a length $L_A$, see FIG. 17, which is a cross-sectional view taken along view line 17-17 in FIG. 16A corresponding to a machine direction. Because the aperture 206 has an ellipse shape, the side wall length $L_4$ is less as compared to an aperture 206 which is generally circular but of substantially similar area. The shorter side wall 212 is advantageous as it is believed to be less likely to buckle or otherwise fold inwardly towards the center of the aperture 206 when compressive forces are applied to the topsheet 206. The aperture side wall 212 may have a length $L_4$ in the range of 0.2 mm to about 2 mm, or in the range of 0.5 mm to about 1.5 mm, according to the 2D X-Ray CT Scan Test herein.

Additional Example Apertures

Figure 20:
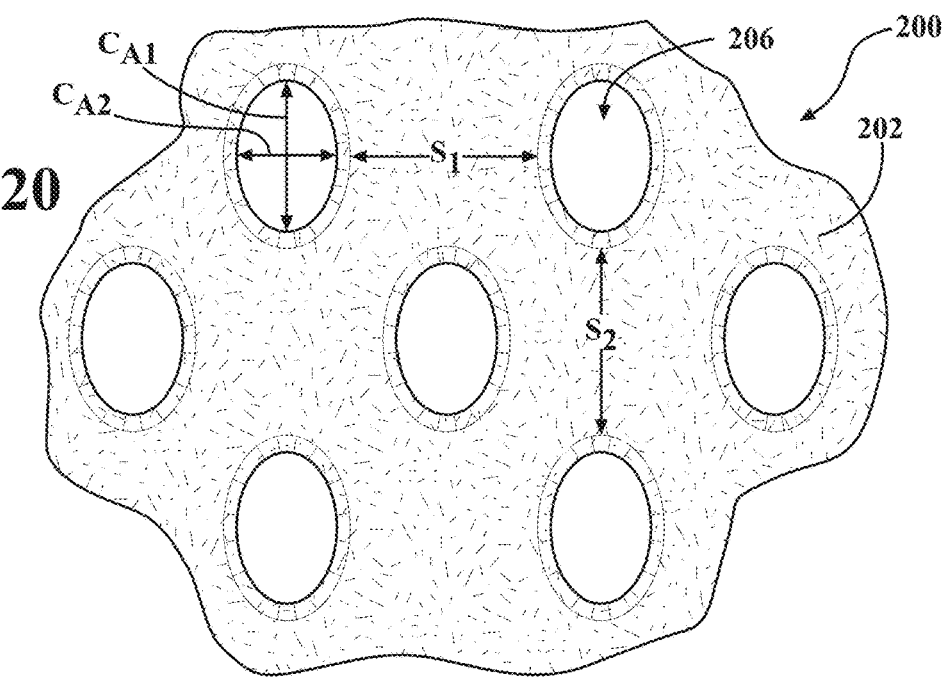
FIGS. 20-22 are views similar to FIG. 19 showing respective pluralities of example apertures in substrates.
Figure 21:
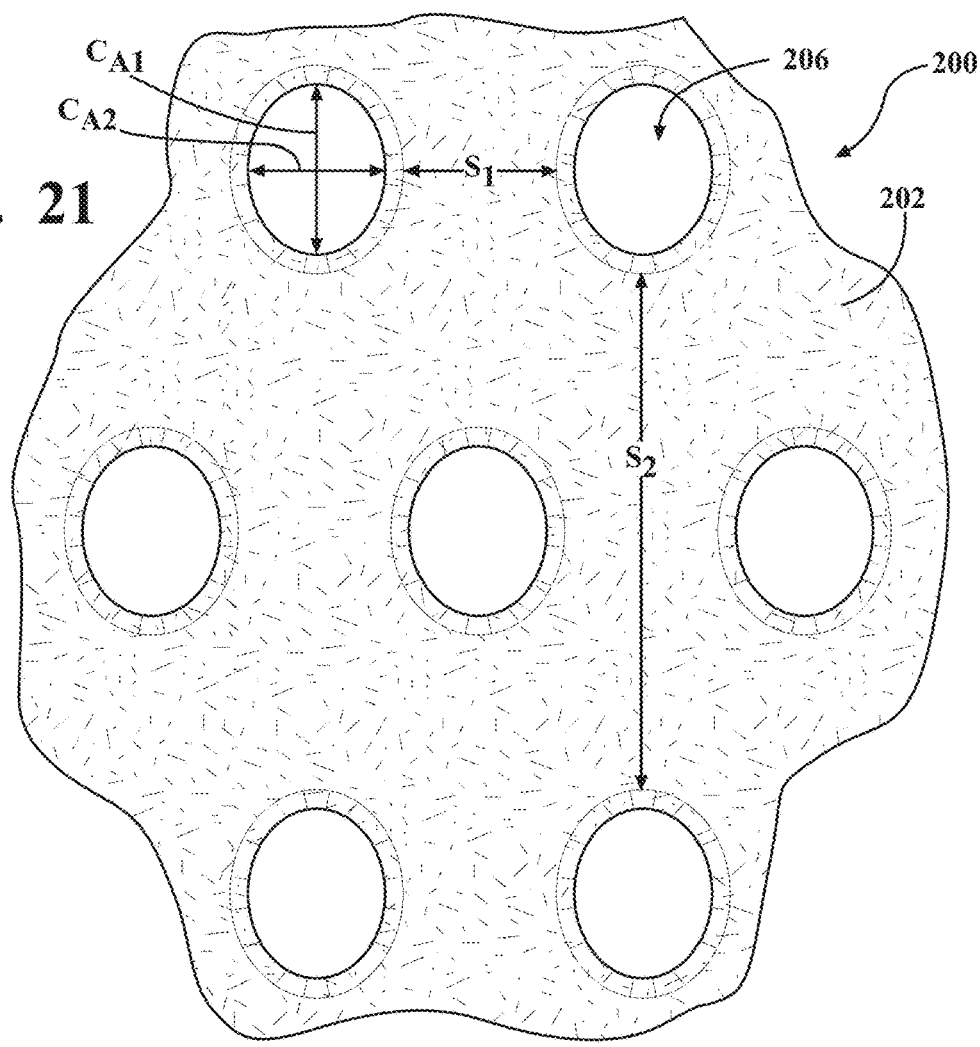
Figure 22:
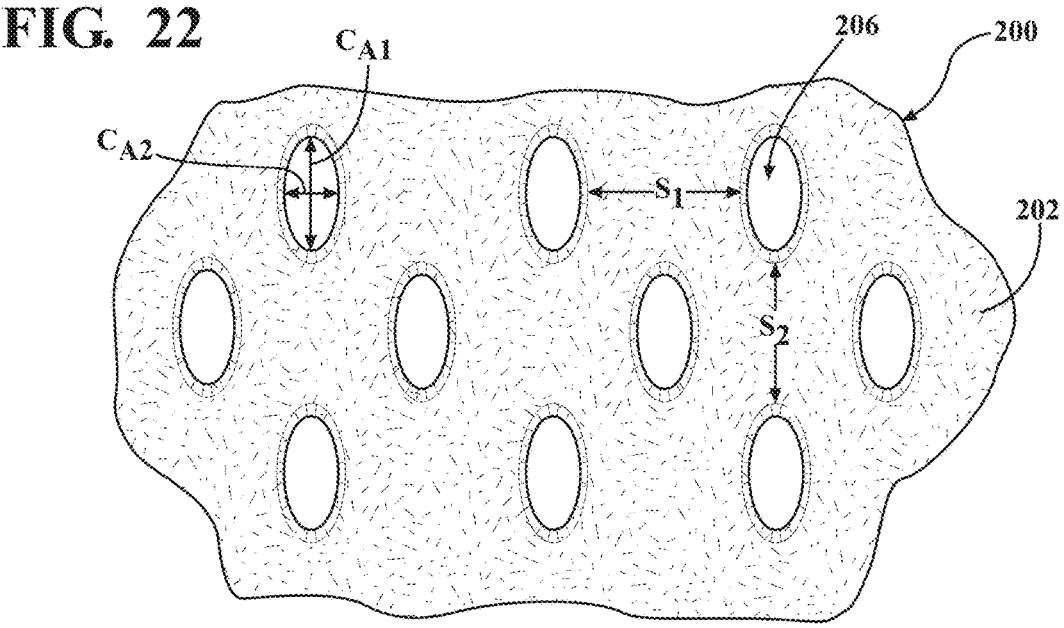

FIGS. 20-22 are views similar to FIG. 19 and show additional example apertures 206 formed in respective topsheets 200. Unless otherwise noted, the material and configuration of the topsheet 200 illustrated in FIGS. 20-22 may be substantially similar to the topsheet 200 described above, and like reference numerals identify like elements.

In FIG. 20, the apertures 206 may be arranged in the topsheet 200 such that the topsheet 200 has an Effective Open Area of about 31%, as measured at the garment-facing surface 204, according to the Aperture Test herein. Such an Effective Open Area may be accomplished with a first spacing $S_1$ in a first direction (a side-to-side direction as shown in FIG. 20) between adjacent apertures 206, as measured at the wearer-facing surface 202, of about 3.0 mm and a second spacing $S_2$ in a second direction (an up and down direction as shown in FIG. 20) between adjacent apertures 206, as measured at the wearer-facing surface 202, of about 3.0 mm, where the central major axis dimension $C_{A1}$ of the apertures 206 is about 3.0 mm and the central minor axis dimension $C_{A2}$ of the apertures 206 is about 2.0 mm.

In FIG. 21, the apertures 206 may be arranged in the topsheet 200 such that the topsheet 200 has an Effective Open Area of about 23%, as measured at the garment-facing surface 204, according to the Aperture Test herein. Such an Effective Open Area may be accomplished with a first spacing $S_1$ in a first direction (a side-to-side direction as shown in FIG. 21) between adjacent apertures 206, as measured at the wearer-facing surface 202, of about 2.5 mm and a second spacing $S_2$ in a second direction (an up and down direction as shown in FIG. 21) between adjacent apertures 206, as measured at the wearer-facing surface 202, of about 8.5 mm, where the central major axis dimension $C_{A1}$ of the apertures 206 is about 3.4 mm and the central minor axis dimension $C_{A2}$ of the apertures 206 is about 2.8 mm.

In FIG. 22, the apertures 206 may be arranged in the topsheet 200 such that the topsheet 200 has an Effective Open Area of about 22%, as measured at the garment-facing opening area 210, according to the Aperture Test herein. Such an Effective Open Area may be accomplished with a first spacing $S_1$ in a first direction (a side-to-side direction as shown in FIG. 22) between adjacent apertures 206, as measured at the wearer-facing surface 202, of about 3.2 mm and a second spacing $S_2$ in a second direction (an up and down direction as shown in FIG. 22) between adjacent apertures 206, as measured at the wearer-facing surface 202, of about 2.6 mm, where the central major axis dimension $C_{A1}$ of the apertures 206 is about 2.5 mm and the central minor axis dimension $C_{A2}$ of the apertures 206 is about 1.2 mm.

Aperture Formation and Forming Apparatus

Any suitable apparatus and processes for forming the apertures 206 may be utilized. For example, the apertures 206 in the materials of the present disclosure may be formed by hydroforming carded webs, laser cutting, punching with a patterned roll, die cutting, using hot pin methods, overbonding and ring rolling aperturing, as disclosed in U.S. Patent Application Publication No. US 2016/0136014 and U.S. Pat. No. 5,628,097, or other suitable methods. The materials could also be apertured by hand, using a pin punch, for example. Additional example aperturing processes may be used such as described in U.S. Pat. Nos. 9,023,261, 8,158,043, 8,241,543, and 8,679,391.

As one example, with reference to FIGS. 23-25B, a nonwoven, liquid permeable substrate 300 comprising a first surface 300A (facing down in FIG. 23) and a second surface 300B (facing up in FIG. 23) is provided into an aperture forming apparatus 310. The first surface 300A of the substrate may correspond to the wearer-facing surface of the substrate 300, and the second surface 300B of the substrate may correspond to the garment-facing surface of the substrate 300.

The substrate 300 may be preheated before entering the apparatus 310 by means known in the art, such as by radiant heating, forced air heating, convection heating, or by heating over oil-heated rollers. Additionally or alternatively, the pins and/or rollers (to be described below) of the apparatus 310 may be heated so as to heat the substrate 300 while apertures are being formed therein. The heat functions to heat-set formed apertures in the substrate 300. The substrate 300 may also be pre-printed with indicia, designs, logos, or other visible or invisible print patterns. For example, designs and colors can be printed by means known in the art, such as by inkjet printing, gravure printing, flexographic printing, or offset printing, to change the color of at least portions of the substrate 300. In addition to printing, the substrate 300 can be treated with coatings, such as with surfactants, lotions, adhesives, and the like. Treating the substrate 300 can be achieved by means known in the art such as by spraying, slot coating, extruding, or otherwise applying coatings to one or both surfaces.

Figure 23:
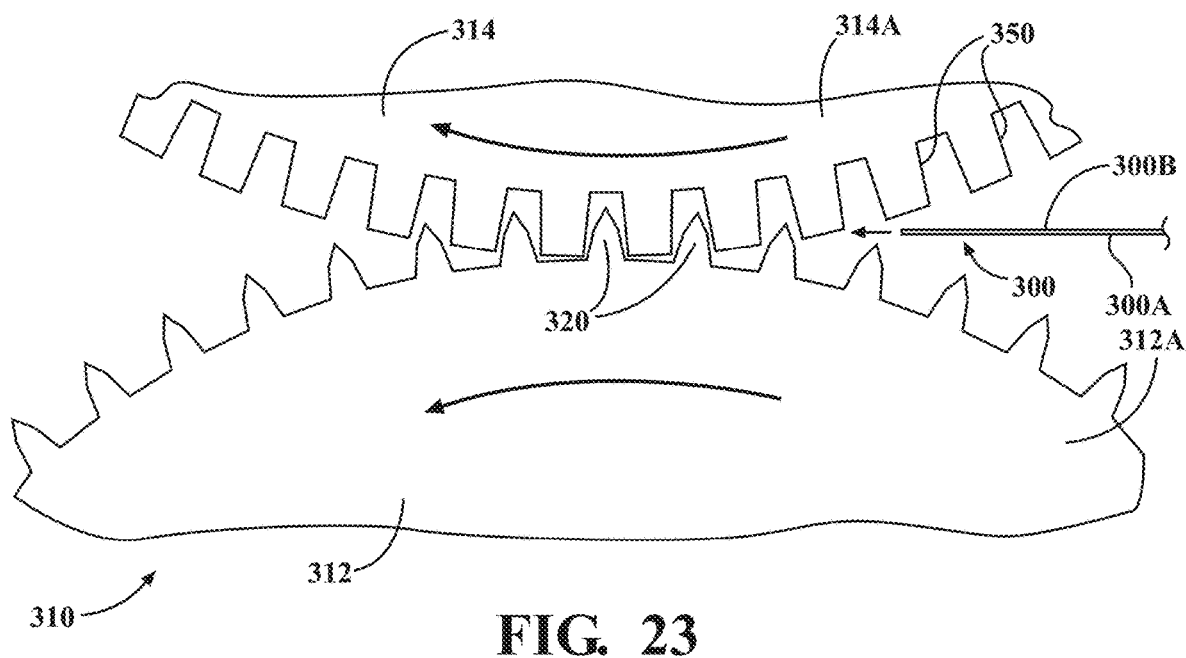
FIG. 23 is a side view of an apparatus for forming apertures in a substrate.

The example apparatus 310 includes a supply apparatus (not show) for moving the substrate 300 in the direction shown in FIG. 23, and a pair of counter-rotating, intermeshing first (lower in FIG. 23 and second (upper in FIG. 23) members comprising rollers 312, 314, each rotating about an axis, the axes being parallel and in the same plane. The rollers 312, 314 can be made of a corrosion resistant and wear resistant material; such as steel or aluminum, and operate to form apertures in the substrate, such as the apertures 206 disclosed herein.

The supply apparatus moves the substrate 300 by means known in the art, including over or around any of various idler rollers, tension-control rollers, and the like (all of which are not shown) to a nip 316 formed by the rollers 312, 314.

The first roller 312 illustrated in FIG. 23 includes a plurality of example pins 320 that are provided to punch through the substrate 300 from the first surface 300A to the second surface 300B to form apertures 206 therein. The pins 320 may have a conical shape or any other suitable shape for forming correspondingly shaped apertures 206 in the substrate 300. The conical-shaped pins 320 may also have a direction of elongation in a machine direction MD, a cross machine direction CD, or a direction between the MD and CD, such as at 45 degrees relative to the MD and CD. In the example pins 320 shown in FIGS. 23-25B, the direction of elongation is in the machine direction MD. "Machine direction" or "MD" is the direction parallel to the direction of travel of the substrate 300 as it moves through the manufacturing process. The "cross machine direction" or "CD" is the direction substantially perpendicular to the MD and in the plane generally defined by the substrate 300.

Figure 25A:
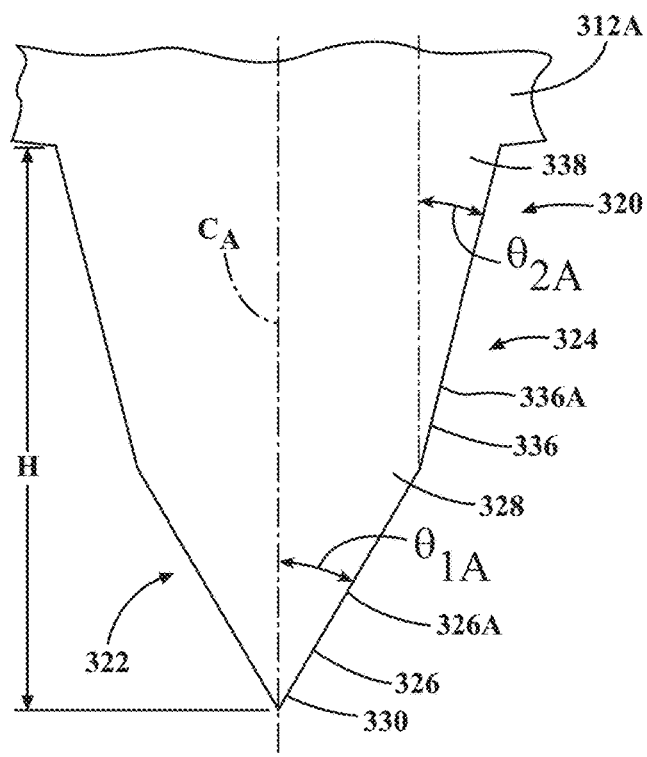
FIGS. 25A and 25B are respective cross sectional views of one of the pins of FIG. 24 taken in the machine and cross machine directions.
Figure 25B:
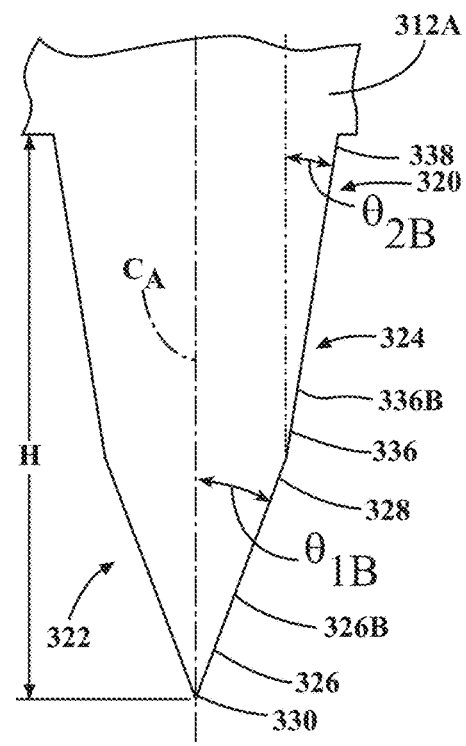

With reference to FIGS. 25A and 25B, the pins 320 may comprise a first section 322 extending outwardly from a second section 324, which second section 324 extends outwardly from a body portion 312A of the first roller 312. FIG. 25A is a cross-sectional view of a pin 320 taken in the machine direction and FIG. 25B is a cross-sectional view of a pin 320 taken in the cross machine direction.

The first section 322 includes a first wall 326 extending from a base portion 328 of the first section 322 to a distal portion 330 of the first section 322, the distal portion 330 defining an outer end/tip of the pin 320. In FIG. 25A, a, first portion 326A of the first wall 326 is disposed at a first machine direction angle $\theta_{1A}$ relative to a central axis $C_A$ of the pin 320, the first direction angle $\theta_{1A}$ being greater than about 17.5 degrees, greater than about 20 degrees, or greater than about 25 degrees. More specifically, with reference to FIG. 25A, the first portion 326A of the pin first section first wall 326 is disposed at a first machine direction angle $\theta_{1A}$ equal to 26.5 degrees. With reference to FIG. 25B, a second portion 326B of the pin first section first wall 326 is disposed at a second cross machine direction angle $\theta_{1B}$, the second direction angle $\theta_{1B}$ being greater than about 17.5 degrees, or greater than about 20 degrees, and less than or equal to the first direction angle $\theta_{1A}$. In the illustrated form, the second cross machine direction angle $\theta_{1B}$ is equal to 20.5 degrees.

The second section 324 includes a second wall 336 extending from a base portion 338 of the second section 324 to the base portion 328 of the first section 322, the second section base portion 338 extending outwardly from the body portion 312A of the first roller 312. A first portion 336A of the second wall 336 is disposed at a third machine direction angle $\theta_{2A}$ relative to the central axis $C_A$ of the pin 320, the third angle $\theta_{2A}$ being less than about 20 degrees, less than about 18 degrees, or less than about 16 degrees. In the illustrated form, the third machine direction angle $\theta_{2A}$ is equal to 14 degrees. A second portion 336B of the second wall 336 is disposed at a fourth cross machine direction angle $\theta_{2B}$ relative to the central axis $C_A$ of the pin 320, the fourth angle $\theta_{2B}$ being less than about 20 degrees, less than about 18 degrees, or less than about 16 degrees. In the illustrated form, the fourth machine direction angle $\theta_{2B}$ is equal to 14 degrees. The pins 320 illustrated in FIGS. 25A and 25B may be drawn with angles $\theta_{1A}$, $\theta_{2A}$, $\theta_{1B}$, $\theta_{2B}$ that differ from the angle values discussed herein for ease of illustration.

As the substrate 300 is conveyed through the apparatus 302, the pins 320 are inserted through the substrate 300 and are received in female notches 350 formed in a body portion 314A of the second roller 314. The pins 320 thus penetrate the substrate 300 from the first surface 300A to the second surface 300B to form apertures 206 therein according to the size and shape of the second sections 324 of the pins 320. For example, the second sections 324 of the pins 320 may define the shapes of the apertures 206, while the first sections 322 of the pins 320 are provided to punch through the substrate 300. The transition in the angles of the pins 320 from the first section 322 to the second section 324 is provided to avoid pins that are substantially longer than the ones shown. More specifically, the pin 320 illustrated in FIGS. 25A and 25B has a height H defined by the first section 322 and the second section 324 of no more than about 5 mm, no more than about 4.5 mm, or no more than about 4 mm. Without the transition in angles of the pins 320 from the first section 322 to the second section 324, in order to achieve aperture side walls having the desired dimensions, i.e., as set by the angles $\theta_{2A}$ and $\theta_{2B}$ of the pin second section 324, the height of the pins 320 would have to be much longer, which would be undesirable as longer pins tend to be less durable and are difficult to release from corresponding female notches 350 in the second roller 314.

Figure 26A:
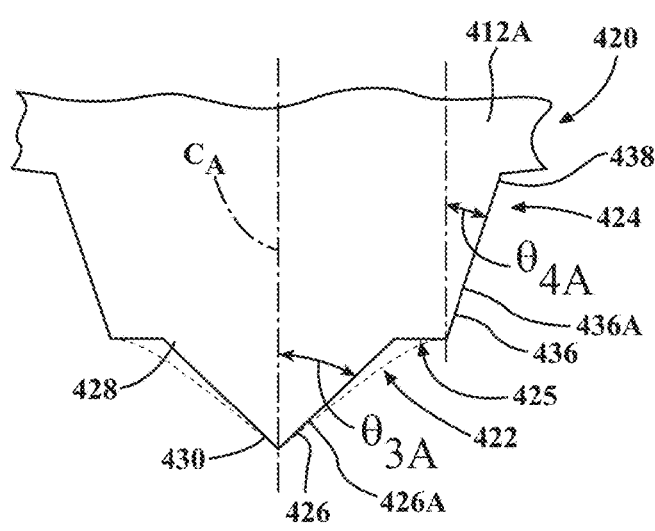
FIGS. 26A and 26B are respective front and side cross sectional views other example pins for forming apertures in a substrate.
Figure 26B:
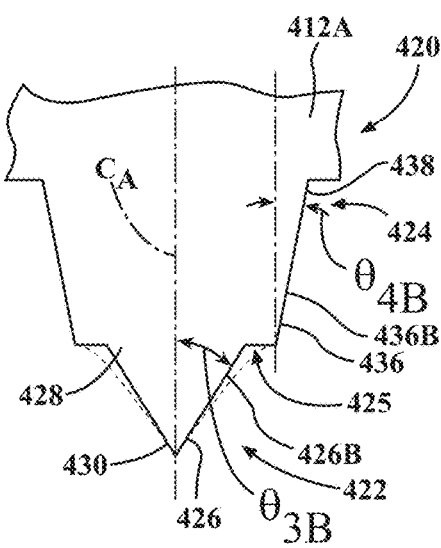

A pin 420 formed in accordance with a further aspect is illustrated in FIGS. 26A and 26B. The pins 420 may be used in place of the pins 320 on the first roller for forming apertures 206 in the substrate 300. The pins 420 comprise a first section 422, a second section 424, and third transitional section 425 extending between the first and second sections 422 and 424. FIG. 26A is a cross-sectional view of a pin 420 taken in the machine direction and FIG. 26B is a cross-sectional view of a pin 420 taken in the cross machine direction.

The pin first section 422 includes a first wall 426 extending from a base portion 428 of the first section 422 to a distal portion 430 of the first section 422, the distal portion 430 defining an outer end/tip of the pin 420. In FIG. 26A, a first portion 426A of the first wall 326 is disposed at a first machine direction angle $\theta_{3A}$ relative to a central axis $C_A$ of the pin 420, the first angle $\theta_{3A}$ being greater than about 17.5 degrees, greater than about 20 degrees, or greater than about 25 degrees. More specifically, with reference to FIG. 26A, the first portion 426A of the pin first section first wall 426 is disposed at a first machine direction angle $\theta_{3A}$ equal to 26.5 degrees. With reference to FIG. 26B, a second portion 426B of the pin first section first wall 426 is disposed at a second cross machine direction angle $\theta_{3B}$, the second direction angle $\theta_{3B}$ being greater than about 17.5 degrees or greater than about 20 degrees, and less than or equal to the first direction angle $\theta_{3A}$. In the illustrated form, the second cross machine direction angle $\theta_{3B}$ is equal to 20.5 degrees.

The second section 424 includes a second wall 436 extending from a base portion 438 of the second section 424 to the base portion 428 of the first section 422, the second section base portion 438 extending outwardly from the body portion 412A of the first roller. A first portion 436A of the second wall 436 is disposed at a third machine direction angle $\theta_{4A}$ relative to the central axis $C_A$ of the pin 420, the third angle $\theta_{4A}$, being less than about 20 degrees, less than about 18 degrees, or less than about 16 degrees. In the illustrated form, the third machine direction angle $\theta_{4A}$ is equal to 14 degrees. A second portion 436B of the second wall 436 is disposed at a fourth cross machine direction angle $\theta_{4B}$ relative to the central axis $C_A$ of the pin 420, the fourth angle $\theta_{4B}$ being less than about 20 degrees, less than about 18 degrees, or less than about 16 degrees. As illustrated, the fourth machine direction angle $\theta_{4B}$ is equal to 14 degrees.

In accordance with yet another aspect of the disclosure, the first wall of the pin first section may define a curved surface extending from the distal portion toward the first section base portion, as shown in phantom lines in FIGS. 26A and 26B.

Examples

A group of topsheet samples formed in accordance with the present disclosure was tested without pressure being applied to the samples and with 689 Pa of pressure being applied to the samples using a GE phoenix v|tome|x m X-ray microfocus CT system. The materials tested were 22 gsm carded air through nonwoven materials with 2 dpf PE/PET sheath/core hydrophobic bicomponent fibers, having a thickness of 0.71 mm. Measurements were performed on 2D x-ray slices in both the MD and CD. Data collected for each sample included aperture diameter, side wall angle, aperture surface area and remaining aperture surface area. The surface area was calculated using the equation:

Aperture Surface area=$\pi$ (a/2)*(b/2), where a, b are the long and short diameters of the aperture, respectively.

An average of the data collected for the first group of topsheet samples without pressure being applied, labeled "sample_1small_pore_average" is set out below. An average of the data collected for the first group of topsheet samples with 689 Pa of pressure being applied, labeled "sample_1_small_pore_under_pressure_average" is set out below.

| measurement | back-side pore diameter in CD (mm) | skin side pore diameter in CD (mm) |
|---|---|---|
| sample_1_small pore_average | 1.20 | 2.17 |
| sample_1_small pore_under pressure_average | 1.09 | 1.98 |

| measurement | back-side pore diameter in MD (mm) | skin side pore diameter in MD (mm) |
|---|---|---|
| sample_1_small pore_average | 2.24 | 2.86 |
| sample_1_small pore_under pressure_average | 2.33 | 2.92 |

| measurement | slope angle in CD (degree) | slope angle in MD (degree) | back-side area (mm2) | skin-side area (mm2) | back-side area remain percentage | skin-side area remain percentage |
|---|---|---|---|---|---|---|
| sample_1_small pore_average | 63.68 | 72.47 | 2.12 | 4.88 | 93.9% | 92.6% |
| sample_1_small pore_under pressure_average | | | 1.99 | 4.52 | | |

As is apparent from the data set out above, for the group of topsheet samples formed in accordance with the present disclosure, the garment and wearer-facing opening areas (i.e., the back-side area and skin-side area) changed only slightly, decreased slightly to 93.9% of the original, uncompressed back-side opening area (back-side area remain percentage in the above chart) and 92.6% of the original, uncompressed skin-side opening area (skin-side area remain percentage in the above chart), when pressure was applied to the samples.

Also, as shown in 2D x-ray slices in the MD of FIG. 27, a topsheet sample 1, formed in accordance with the present disclosure, had very little if any aperture closure when the sample was subjected to pressure.

Test Methods

Unless indicated otherwise, all tests described herein are made with samples conditioned at least 24 hours at 23° C.±2° C. and 50%±10% Relative Humidity (RH).

Basis Weight Test

Basis weight of the materials disclosed herein may be determined by several available techniques, but a simple representative technique involves taking an absorbent article or other consumer product, removing any elastic which may be present and stretching the absorbent article or other consumer product to its full length. A punch die having an area of 45.6 cm² is then used to cut a piece of the patterned apertured web (e.g., topsheet, outer cover) from the approximate center of the absorbent article or other consumer product in a location which avoids to the greatest extent possible any adhesive which may be used to fasten the patterned apertured web to any other layers which may be present and removing the patterned apertured web from other layers (using cryogenic spray, such as Cyto-Freeze, Control Company, Houston, Tex., if needed). The sample is then weighed and dividing by the area of the punch die yields the basis weight of the patterned apertured web. Results are reported as a mean of 5 samples to the nearest 0.1 cm².

Aperture Test

Aperture dimensions, Effective Aperture Area, % Effective Open Area, among other measurements, are obtained from specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach Calif. or equivalent). The scanner is interfaced with a computer running an image analysis program (a suitable program is ImageJ v. 1.47 or equivalent, National Institute of Health, USA). The specimen images are distance calibrated against an acquired image of a ruler certified by NIST. A steel frame is used to mount the specimen, which is then backed with a black glass tile (P/N 11-0050-30, available from HunterLab, Reston, Va.) prior to acquiring the specimen image. The resulting image is then threshold, separating open aperture regions from specimen material regions, and analyzed using the image analysis program. All testing is performed in a conditioned room maintained at about 23±2° C. and about 50±2% relative humidity.

Sample Preparation:

To obtain a specimen, tape an absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen. Take the steel frame and place double-sided adhesive tape on the bottom surface surrounding the interior opening. Remove the release paper of the tape, and adhere the steel frame to the apertured layer of the article. Align the frame so that it is parallel and perpendicular to a machine direction (MD) and a cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston Tex.) may be used to remove the specimen from the underlying layers if necessary. Five replicates obtained from five substantially similar articles are prepared for analysis. If the apertured layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. An apertured or patterned apertured substrate raw material is prepared for testing by extending or activating it under the same process conditions, and to the same extent, as it would be for use on the absorbent article, and then in its extended state adhering it to the steel frame as described above for testing. Condition the samples at about 23° C.±2 C.° and about 50%±2% relative humidity for 2 hours prior to testing.

Image Acquisition:

Place the ruler on the scanner bed, oriented parallel to sides of the scanner glass, and close the lid. Acquire a calibration image of the ruler in reflectance mode at a resolution of 6400 dpi (approximately 252 pixels per mm) and 8 bit grayscale, with the field of view corresponding to the dimensions of an interior of the steel frame. Save the calibration image as an uncompressed TIFF format file. Lift the lid and remove the ruler. After obtaining the calibration image, all specimens are scanned under the same conditions and measured based on the same calibration file. Next, place the framed specimen onto the center of the scanner bed, lying flat, with the outward facing surface of the specimen facing the scanner's glass surface. Orient the specimen so that sides of the frame are aligned parallel with and perpendicular to the sides of the scanner's glass surface, so that the resulting specimen image will have the MD vertically running from top to bottom. Place the black glass tile on top of the frame covering the specimen, close the lid and acquire a scanned image. Scan the remaining four replicates in like fashion. If necessary, crop all images to a rectangular field of view circumscribing the apertured region, and resave the files.

% Effective Open Area Calculation:

Open the calibration image file in the image analysis program and perform a linear distance calibration using the imaged ruler. This distance calibration scale will be applied to all subsequent specimen images prior to analysis. Open a specimen image in the image analysis program and set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image the apertures appear as black, with a GL value of 255, and specimen as white, with a GL value of 0.

Using the image analysis program, analyze each of the discrete aperture regions. Measure and record all of the individual aperture areas to the nearest 0.01 mm², including partial apertures along the edges of the image. Discard any apertures with an area less than 0.3 mm² as "non-effective". Sum the remaining aperture areas (including whole and partial apertures), divide by the total area included in the image and multiply by 100. Record this value as the % effective open area to the nearest 0.01%.

In like fashion, analyze the remaining four specimen images. Calculate and report the average % effective open area values to the nearest 0.01% for the five replicates.

2D X-Ray CT Scan Test

The CT data presented herein were collected on topsheet samples with or without pressure (around 289 Pa). The samples were mounted parallel to the X-ray beam direction on a plastic sample holder with a foam surface (low X-ray absorption). Specimens from articles are prepared in the same fashion as done for the Aperture Test measurement above and are approximately 2.0 cm×2.0 cm. The sample holder was then fixed on a rotational stage (integrated within the machine chamber) and scanned using a GE Phoenix v|tome|x m CT scanner (GE Sensing & Inspection Technologies GmbH Niels-Bohr-Str.7 31515 Wunstorf, Germany) with the following image acquisition parameters to ensure good image quality: micro-tube; voltage: 30 kV; current: 500 µA; tube mode: 1; timing: 1000 ms; averaging: 2; skip frames: 1; number of images: 1500. Each reconstructed data set consists of a stack of 2D images, each 2014*2014 pixels, with an isotropic resolution of 11.48 µm/voxel. The 3D reconstructions were performed using the software accompanying the GE CT instrument.

Visualization, image analysis, and quantification were done using the software VG Studio MAX 3.0 (Volume Graphics GmbH, Germany), Avizo 9.1.1 (Visualization Services Group/FEI Company, Burlington, Mass., U.S.A.) and image J. Image visualization of the Micro-CT data comprised of the following steps:

1. The reconstructed Micro-CT data was read into VG studio MAX 3.0.
2. Export the 3D CT data set to 16 bit tif image stack using VG Studio MAX 3.0.
3. The 16 bit tif image stack was then read into Avizo 9.1.1.
4. A thresholding method based on the image gray level was used to segment the top sheet from the background.
5. After thresholding, the 3D surfaces of the top sheet samples were generated using the generate surface module with a smooth parameter of 3.

Figure 28:
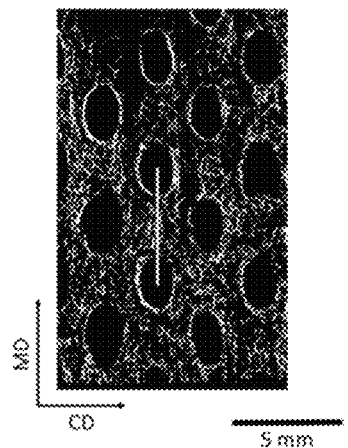
FIG. 28 is a view showing a pore pattern distance measurement in accordance with a 2D X-Ray CT Scan Test as disclosed herein.
Figure 29:
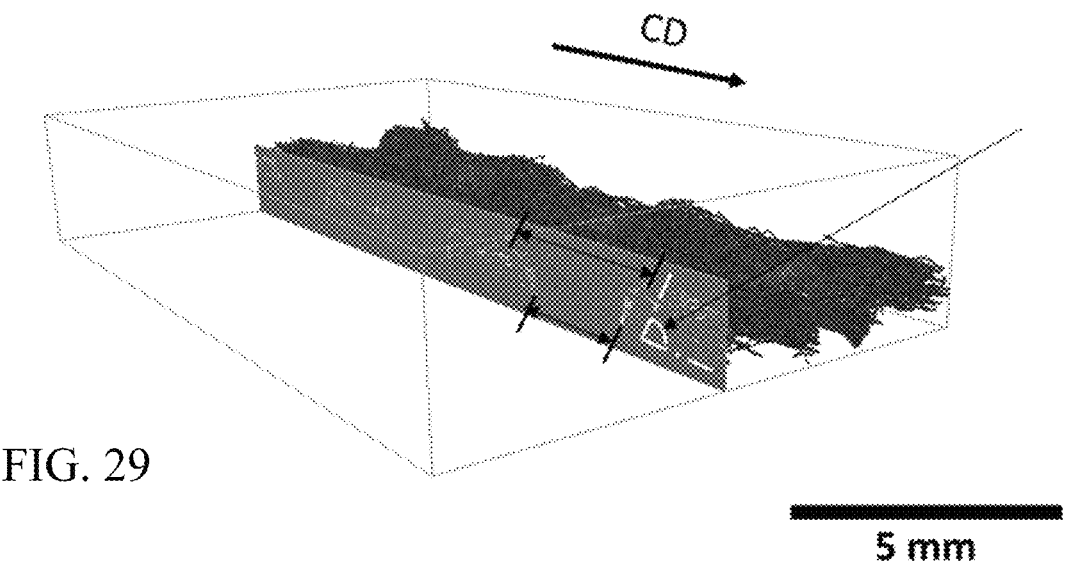
FIG. 29 is a view showing a pore size and angle measurement in accordance with the 2D X-Ray CT Scan Test as disclosed herein.

Image analysis and quantification of the Micro-CT data comprised of the following steps:

1. The image stacks generated by VG studio MAX 3.0 were imported into image J.
2. The pore pattern distance measurements were performed on the X-ray CT slices parallel to the MD and CD axis as shown in FIG. 28. For each sample the distances of pore centers (indicated by the line in FIG. 28) in both MD and CD are measured as a reflection of their pattern.
3. The image stacks were then resliced in image J (reslice module) along MD and CD axis into 2D X-ray CT slices for pore size and angle measurement.
4. The pore size in both skin side and back side were then measured on the center X-ray CT slices of each pore along MD and CD axis as shown in FIG. 29. The angle between the line parallel to the top sheet fiber of the pore and the line parallel to the MD and CD plane were measured as an indication of the pore surface angle, as shown by the dashed line in FIG. 29.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any aspect disclosed or claimed herein or that it alone, or in any combination with any other reference or references, teaches, suggests or discloses any such aspect. Further, to the extent that any meaning or definition of a term in this document conflicts with any meaning or definition of the same term in a document incorporated by reference, the meaning or definition assigned to that term in this document shall govern.

While particular aspects of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. An absorbent article comprising:
a nonwoven, liquid permeable topsheet;
a liquid impermeable backsheet; and
an absorbent core disposed at least partially intermediate the topsheet and the backsheet;
wherein the topsheet comprises:
a layer of fibers;
wherein the Basis Weight of the topsheet is in the range of about 10 gsm to about 35 gsm, according to the Basis Weight Test herein;
a plurality of apertures defined in the layer of fibers;
wherein the topsheet has an Effective Open Area in the range of about 15% to about 30%, according to the Aperture Test herein;
wherein the topsheet comprises a wearer-facing surface and a garment-facing surface;
wherein at least some of the apertures have a wearer-facing opening area and a garment-facing opening area, wherein the wearer-facing opening area extends in a first plane, wherein the garment-facing opening area extends in a second plane, wherein the first plane is parallel to the second plane, wherein the wearer-facing opening area is positioned directly opposite the garment-facing opening area, and wherein the wearer-facing opening area is larger than the garment-facing opening area;
wherein at least some of the apertures comprise a side wall, wherein at least a portion of the side wall has an angle in the range of about 55 degrees to about 90 degrees, according to the 2D X-Ray CT Scan Test herein, and wherein the garment-facing opening area is not formed in the side wall;
wherein the garment-facing opening area of at least some of the apertures is in the range of about 1.0 mm$^2$ to about 7.5 mm$^2$, according to the 2D X-Ray CT Scan Test herein;
wherein the wearer-facing opening area of at least some of the apertures is in the range of about 2 mm$^2$ to about 12 mm$^2$, according to the 2D X-Ray CT Scan Test herein; and
wherein at least some of the apertures have a central major axis dimension and a central minor axis dimension, and wherein the central major axis dimension is greater than 1.5 mm, when measured at the garment-facing opening area, according to the 2D X-Ray CT Scan Test herein.

2. The absorbent article of claim 1, wherein at least some of the fibers comprise bicomponent fibers comprising a core and a sheath.

3. The absorbent article of claim 2, wherein the sheath comprises polyethylene, and wherein the core comprises polyethylene terephthalate.

4. The absorbent article of claim 1, wherein a ratio of the central major axis dimension to the central minor axis dimension is at least 1.3, but less than 4, when measured at the garment-facing opening area, according to the 2D X-Ray CT Scan Test herein.

5. The absorbent article of claim 1, wherein at least some of the fibers have a denier per filament of about 1 to about 3.

6. The absorbent article of claim 1, wherein the central major axis dimension is in the range of about 2.0 mm to about 3.0 mm, when measured at the garment-facing opening area, according to the 2D X-Ray CT Scan Test herein.

7. The absorbent article of claim 1, wherein the central minor axis dimension is in the range of about 0.5 mm to about 2.5 mm, when measured at the garment-facing opening area, according to the 2D X-Ray CT Scan Test herein.

8. The absorbent article of claim 1, wherein at least some of the side walls of the apertures have a length in the range of 0.2 mm to about 2.0 mm, according to the 2D X-Ray CT Scan Test herein.

9. The absorbent article of claim 1, wherein the layer of fibers is hydrophobic.

10. The absorbent article of claim 9, wherein the topsheet comprises a second layer, and wherein the second layer is hydrophilic.

11. The absorbent article of claim 1, wherein layer of fibers comprises carded fibers.

12. The absorbent article of claim 1, wherein the layer of fibers comprises spunbond fibers.

13. The absorbent article of claim 1, wherein the topsheet comprises cotton.

14. The absorbent article of claim 1, wherein the topsheet is free of a film.

15. The absorbent article of claim 1, wherein the Basis Weight of the topsheet is in the range of about 18 gsm to about 25 gsm, wherein the Effective Open Area is in the range of about 18% to about 25%, and wherein the portion of the side wall has an angle in the range of about 60 degrees to about 80 degrees.

16. The absorbent article of claim 1, wherein the topsheet comprises a second layer, wherein the second layer is hydrophilic.

17. An absorbent article comprising:
a nonwoven, liquid permeable topsheet;
a liquid impermeable backsheet; and
an absorbent core disposed at least partially intermediate the topsheet and the backsheet;
wherein the topsheet comprises:
a layer of hydrophobic, carded fibers;
wherein the Basis Weight of the topsheet is in the range of about 10 gsm to about 35 gsm, according to the Basis Weight Test herein;
a plurality of apertures defined in the layer of carded fibers;
wherein the topsheet has an Effective Open Area in the range of about 15% to about 30%, according to the Aperture Test herein;
wherein the topsheet comprises a wearer-facing surface and a garment-facing surface;
wherein at least some of the apertures have a wearer-facing opening area and a garment-facing opening area, wherein the wearer-facing opening area extends in a first plane, wherein the garment-facing opening area extends in a second plane, wherein the first plane is parallel to the second plane, wherein the wearer-facing opening area is positioned directly opposite the garment-facing opening area, and wherein the wearer-facing opening area is larger than the garment-facing opening area;

wherein at least some of the apertures comprise a side wall, and wherein at least a portion of the side wall has an angle in the range of about 55 degrees to about 90 degrees, according to the 2D X-Ray CT scan Test herein;

wherein the garment-facing opening area of at least some of the apertures is in the range of about 1.0 mm² to about 7.5 mm², according to the 2D X-Ray CT Scan Test herein;

wherein the wearer-facing opening area of at least some of the apertures is in the range of about 2 mm² to about 12 mm², according to the 2D X-Ray CT Scan Test herein; and wherein at least some of the apertures have a central major axis dimension and a central minor axis dimension, and wherein the central major axis dimension is greater than 1.5 mm, when measured at the garment-facing opening area, according to the 2D X-Ray CT Scan Test herein.

18. The absorbent article of claim 17, wherein the topsheet comprises a layer of spunbond fibers.

19. The absorbent article of claim 17, wherein the topsheet comprises cotton.

20. The absorbent article of claim 17, wherein the Basis Weight of the topsheet is in the range of about 18 gsm to about 25 gsm, and wherein the Effective Open Area is in the range of about 18% to about 25%.

21. The absorbent article of claim 17, wherein the portion of the side wall has an angle in the range of about 60 degrees to about 80 degrees.

22. An absorbent article comprising:
a nonwoven, liquid permeable topsheet;
a liquid impermeable backsheet; and
an absorbent core disposed at least partially intermediate the topsheet and the backsheet;
wherein the topsheet comprises:
a layer of fibers;
wherein the Basis Weight of the topsheet is in the range of about 18 gsm to about 25 gsm, according to the Basis Weight Test herein;
a plurality of apertures defined in the layer of fibers;
wherein the topsheet has an Effective Open Area in the range of about 18% to about 25%, according to the Aperture Test herein;
wherein the topsheet comprises a wearer-facing surface and a garment-facing surface;
wherein at least some of the apertures have a wearer-facing opening area and a garment-facing opening area, wherein the wearer-facing opening area extends in a first plane, wherein the garment-facing opening area extends in a second plane, wherein the first plane is parallel to the second plane, wherein the wearer-facing opening area is positioned directly opposite the garment-facing opening area, and wherein the wearer-facing opening area is larger than the garment-facing opening area;
wherein at least some of the apertures comprise a side wall, and wherein at least a portion of the side wall has an angle in the range of 60 degrees to about 80 degrees, according to the 2D X-Ray CT Scan Test herein;
wherein the garment-facing opening area of at least some of the apertures is in the range of about 1.0 mm² to about 7.5 mm², according to the 2D X-Ray CT Scan Test herein;
wherein the wearer-facing opening area of at least some of the apertures is in the range of about 2 mm² to about 12 mm², according to the 2D X-Ray CT Scan Test herein; and
wherein at least some of the apertures have a central major axis dimension and a central minor axis dimension, and wherein the central major axis dimension is greater than 1.5 mm, when measured at the garment-facing opening area, according to the 2D X-Ray CT Scan Test herein.

* * * * *